United States Patent [19]
Gleich et al.

[11] Patent Number: 6,071,910
[45] Date of Patent: Jun. 6, 2000

[54] USE OF AGENTS TO TREAT EOSINOPHIL-ASSOCIATED PATHOLOGIES

[75] Inventors: Gerald J. Gleich; Jennifer L. Bankers-Fulbright, both of Rochester, Minn.

[73] Assignee: Mayo Foundation for Medical Education and Research, Rochester, Minn.

[21] Appl. No.: 08/985,613

[22] Filed: Dec. 5, 1997

Related U.S. Application Data

[60] Provisional application No. 60/032,416, Dec. 5, 1996.

[51] Int. Cl.$^7$ .......................... A01N 47/34; A61K 31/175
[52] U.S. Cl. ..................................... 514/235.5; 514/237.2; 514/255; 514/299; 514/563; 514/592; 514/593; 514/825; 514/885; 435/1; 435/2; 435/3; 435/240.1; 435/240.2; 435/244; 435/243; 435/260; 435/962
[58] Field of Search .............................. 514/235.5, 237.2, 514/255, 299, 563, 592, 593; 825/885; 435/2, 1, 3, 240.1, 240.2, 244, 243, 260, 962

[56] References Cited

U.S. PATENT DOCUMENTS

| | | | |
|---|---|---|---|
| 4,466,973 | 8/1984 | Rennie | 424/121 |
| 4,626,530 | 12/1986 | Schulte | 514/166 |
| 4,748,022 | 5/1988 | Busciglio | 424/195.1 |
| 5,134,166 | 7/1992 | Bernstein | 514/627 |
| 5,243,922 | 9/1993 | Welsh et al. | 514/223.2 |
| 5,510,339 | 4/1996 | Gleich et al. | 514/171 |
| 5,631,267 | 5/1997 | Gleich et al. | 514/312 |

OTHER PUBLICATIONS

"Airways Obstruction—Bronchial Asthma", *Merck Manual*, 14th Edition, R. Berkow (ed.), Merck Sharp and Dohme Research Laboratories, 622–627, (1982).

"Remington's Pharmaceutical Sciences", 17th Ed., A.R. Gennaro et al. (eds.) Philadelphia College of Pharmacy and Science, 1051–1052, (1985).

Ayars, G.H., et al., "Injurious Effect of the Eosinophil Peroxide–Hydrogen Peroxide–Halide System and Major Basic Protein on Human Nasal Epithelium in vitro", *Am. Rev. Resp. Dis.*, 140, 125–131, (1989).

Barnes, P.J., "The Lancet", 242, (Feb. 1, 1986).

Bascom, R., et al., "Major Basic Protein and Eosinophil–Derived Neurotoxin Concentrations in Nasil–Lavage Fluid After Antigen Challenge: Effect of Systemic Corticosteroids and Relationship to Eosinophil Influx", *J. Allergy Clin. Immunol.*, 84, 338–346, (1989).

Butterfield, J.H., et al., "Chapter 8: Anti–Inflammatory Effect of Glucocorticoids on Eosinophils and Neutrophils", *Anti–Inflammatory Steriod Action: Basic and Clinical Aspects.*, Schleimer et al., editors, Academic Press Inc., 151–198, (1980).

Chen, W.Y., et al., "Effects of Inhaled Lidocaine on Exercise–Induced Asthma", *Respiration*, 51, 91–97, (1987).

Downes, H., et al., "Lidocaine Aerosols Do Not Prevent Allergic Bronchoconstriction", *Anesth. Analg.*, vol. 60, No. 1, 28–32 (1981).

Dunnill, M.S., "The Pathology of Asthma, with Special Reference to Changes in the Bronchial Mucosa", *J. Clin. Path.*, 13, 27–33, (1960).

Enright, P.L., et al., "Am. Rev. Resp. Disease, 172", 823, (1980).

Filley, W.V., et al., "Identification by immunofluorescence of eosinophil granule major basic protein in lung tissues of patients with bronchial asthma", *The Lancet*, 2, 11–16, (1982).

Frigas, E., et al., "Cytotoxic Effects of the Guinea Pig Eosinophil Major Basic Protein on Tracheal Epithelium", *Lab. Invest.*, 42, 35–43, (1980).

Frigas, E., et al., "Elevated Levels of the Eosinophil: Granule Major Basic Protein in the Sputum of Patents with Bronchial Asthma", *Mayo Clinic. Proc.* 56:345, (1981).

Fujisawa, T., et al., "Regulatory Effects of Cytokines on Eosinophil Degranulation", *J. Immunol.*, 144, 642–646, (1990).

Gross, N.J., et al., "Chapter 34: Anticholinergic Drugs", *Allergy, Principles and Practice*, vol. 1, E. Middleton Jr. et al., ed., The C.V. Mosby Company, Publisher, 782–808, (1988).

Gundel, R.H., et al., "Repeated Antigen Inhalation Results in a Prolonged Airway Eosinophilia and Airway Hyperresponsiveness in Primates", *J. Appl. Physiol.*, 68, 779, (1990).

Horn, B.R., et al., "Total Eosinophil Counts in the Management of Bronchial Asthma", *N. Engl. J. Med.*, 292, 1152, (1975).

Kita, et al., *J. Immunol.*, 149, 629, (1992).

Krasnowska, M., et al., "A Test of Lidocaine Usage in the Treatment of Bronchial Asthma", *Pneum. Pol.*, 50, 269–273, (1982).

Lamas, A.M., et al., "Glucocorticoids Specifically Decrease Eosinophil Survival", *J. Allergy Clin. Immunol.* 85, Abstract No. 554, 282, (1990).

Lamas, A.M., et al., "Human Endothelial Cells Prolong Eosinophil Survival", *J. Immunol.*, 142, 3978, (1989).

Mauser, P.J., et al., "The Effect of Anti–Il–5 on Antigen–Induce Airway Hyperreactivity and Pulmonary Eosinophilia in Guinea Pigs", *Am. Rev. Respir. Dis.*, 145, A859, (1992).

Motojima, S., et al., "Toxicity of Eosinophil Cationic Proteins for Guinea Pig Tracheal Epithelium in Vitro", *Am. Rev. Resir. Dis.*, 139, 801, (1989).

(List continued on next page.)

*Primary Examiner*—Frederick Krass
*Attorney, Agent, or Firm*—Schwegman, Lundberg Woessner and Kluth

[57] ABSTRACT

A therapeutic method comprising counteracting or preventing pathologies mediated by IL-5, including those characterized by eosinophil infiltration, degranulation and inflammation, by administering to a mammal in need of such therapy, one or more compounds that bind to the eosinophil sulfonylurea receptor, optionally in combination with one or more topical anesthetics and/or glucocorticoids.

18 Claims, 17 Drawing Sheets

OTHER PUBLICATIONS

Ohnishi, T., et al., "Lidocaine In Bronchoalveolar Lavage Fluid (BALF) Is An Inhibitor of Eosiniphil–Active Cytokines", *Clin. Exp. Immunol.,* 104, 325, (1996).

Rothenberg, M.E., et al., "Human Eosinophil have Prolonged Survival, Enhanced Functional Properties, and Become Hypodense when Exposed to Human Interleukin 3", *J. Clin. Invest.,* 81, 1986, (1988).

Saperov, V.N., "The Treatment of Bronchial Asthma with the Aid of Intra–Arterial Injections of Novocain", *Klin. Med.,* 45, 50–54, (1967).

Schleimer, R.P., et al., "Effects of Glucocorticosteriods on Inflammatory Cells Relevant to Their Therapeutic Applications in Asthma", *Am. Rev. Respir., Dis.,* 141, 559, (1990).

Sedgwick, J.B., et al., "Immediate and Late Airway Response of Allergic Rhinitis Patients to Segmental Antigen Challenge", *Am. Rev. Respir. Dis.,* 144, 1274, (1991).

Sehmi, R., et al., "Interleukin–5 Selectively Enhances the Chemotactics Response of Eosinophils Obtained from Normal but not Eosinophilic Subjects", *Blood,* 79, 2952, (1992).

Silberstein, D.S., et al., "Enhancement of Human Eosinophil Cytoxicity and Leukotriene Synthesis by Biosynthetic (Recombinant) Granulocyte–Macrophage Colony–Stimulating Factor", *J. Immunol.,* 137, 3290, (1986).

Silberstein, D.S., et al., "Hemopoietins for Eosinophils", *Hematol. Oncol. Clin. North Am.,* 3, 511, (1989).

Tullett, W.M., "Thorax, 37", 737, (1982).

Valerius, T., et al., "Effects of IFN on Human Eosinophils in Comparison with Other Cytokines", *J. Immunol,* 145, 2950, (1990).

Wallen, N., et al., "Glucocorticoids Inhibit Cytokine–Mediated Eosinophil Survival", *J. Immunol.,* 147, 3940, (1991).

Wasmoen, T.L., et al., "Biochemical and amino acid sequence analysis of human eosinophil granule major basic protein", *J. of Biol. Chem.,* 263, 12559–12563, (1988).

LIDOCAINE, DEXAMETHASONE AND GLYBURIDE SYNERGIZE TO INHIBIT IL-5
MEDIATED EOSINOPHIL SURVIVAL$^§$

| TREATMENT | EXPECTED SURVIVAL (% CONTROL)$^†$ | ACTUAL SURVIVAL (% CONTROL)$^†$ |
| --- | --- | --- |
| MEDIA CONTROL | – | 100 ± 0 |
| $10^{-3}$M LIDOCAINE | – | 79 ± 5 |
| $10^{-4}$M GLYBURIDE | – | 44 ± 13 |
| $10^{-4}$M DEXAMETHASONE | – | 97 ± 2 |
| $10^{-3}$M LIDOCAINE + $10^{-4}$M GLYBURIDE | 23 ± 12 | 8 ± 6** |
| $10^{-3}$M LIDOCAINE + $10^{-6}$M DEXAMETHASONE | 76 ± 6 | 35 ± 20* |
| $10^{-4}$M GLYBURIDE + $10^{-6}$M DEXAMETHASONE | 41 ± 13 | 21 ± 13** |

$^§$ EOSINOPHIL SURVIVAL WAS ASSAYED AS DESCRIBED IN *METHODS* AND IS LISTED AS A PERCENTAGE OF THE EOSINOPHIL SURVIVAL AT 1000 pg/ml IL-5 IN THE ABSENCE OF DRUG, DEFINED AS 100%. ALL TREATMENTS ARE IN THE PRESENCE OF 1000 pg/ml IL-5.

$^†$EXPECTED SURVIVAL VALUES REPRESENT THE PREDICTED ADDITIVE EFFECT OF THE DRUGS BASED ON THEIR INDIVIDUAL EFFECTS. ACTUAL SURVIVAL VALUES ARE THE EXPERIMENTAL VALUES ACTUALLY OBTAINED WHEN DRUG COMBINATIONS WERE USED.

USE OF AGENTS TO TREAT EOSINOPHIL-ASSOCIATED PATHOLOGIES

CROSS-REFERENCE TO RELATED APPLICATION

This application claims the benefit under 35 U.S.C. §119 (e) of U.S. Provisional Patent Application Ser. No. 60/032, 416, filed on Dec. 5, 1996, which is incorporated herein by reference.

GOVERNMENT SUPPORT

This invention was made with the assistance of the United States Public Health Service, National Institutes of Health, under grant number AI-07047. The U.S. Government has certain rights in the invention.

BACKGROUND OF THE INVENTION

The eosinophil is an effector cell in the pathophysiology of a wide variety of diseases. Eosinophils possess and/or produce toxic basic proteins, e.g., major basic protein (MBP) and eosinophil-cationic protein (ECP), which they are able to deposit on their targets. They also possess and/or produce toxic oxygen metabolites, including $H_2O_2$, and hypohalous acids, including hypobromous acid. For example, hypobromous acid is a potent oxidant that is generated by the eosinophil peroxidase $(EPO)+H_2O_2+Br^-$. The ability of the eosinophil to kill targets can be increased by activators produced by other cells, such as T lymphocytes. These other cells can synthesize a series of glycoprotein hormones that regulate eosinophil function, including granulocyte-macrophage colony-stimulating factor (GM-CSF), interleukin-3 (IL-3) and IL-5. Information obtained over the past several years has indicated that eosinophils themselves have the ability to produce cytokines, such as GM-CSF, and IL-3. These cytokines can activate the eosinophil itself, in an autocrine fashion.

Eosinophilia is the infiltration of eosinophils into tissues such as blood or lung, and the activation of those eosinophils, which results in the production of eosinophil-derived proteins that in turn mediate pathogenic effects. The infiltration of eosinophils into tissues, and the subsequent degranulation of the eosinophils, is associated with hypersensitivity diseases such as bronchial asthma, chronic eosinophilic pneumonia, vernal conjunctivitis, allergic conjunctivitis, allergic rhinitis, allergic sinusitis, and allergic gastroenteropathy. Examples of other eosinophil-associated diseases include eosinophilic gastroenteritis, atopic dermatitis, bullous pemphigoid, episodic angioedema associated with eosinophilia, and ulcerative colitis. In all of these diseases, evidence exists that the eosinophil plays a significant, if not major role in pathophysiology.

IL-5 is known to play an important role in the regulation of the immune system and is one of several cytokines regulating organ-specific eosinophil infiltration and degranulation during normal host immune finction (Kita et al., *J. Immunol.*, 149, 629 (1992)). Moreover, IL-5, as well as the cytokines IL-3, IFN-γ and GM-CSF, prolong the survival of eosinophils in vitro (Valenus et al., *J. Immunol.*, 145, 2950 (1990)) and augment eosinophil function (Rothenberg et al., *J. Clin. Investig.*, 81, 1986 (1988); Fujisana et al., *J. Immunol.*, 144, 642 (1990); Silberstein et al., *J. Immunol.*, 137, 3929 (1986)). Furthermore, several types of diseases are correlated with IL-5 activity, including parasitic, autoimmune, atopic and malignant diseases.

Ohnishi et al. (*Clin. Exp. Immunol.*, 104, 325 (1996)) disclose that eosinophils in bronchoalveolar lavage (BAL) fluids from some symptomatic asthma patients had enhanced survival that was primarily due to enhanced IL-5 levels. They further disclose that lidocaine, a topical anesthetic which is employed to obtain BAL fluid, was found to inhibit IL-5 mediated eosinophil survival. The treatment of bronchial asthma and other hypersensitivity diseases with topical anesthetics is disclosed in Gleich et at. (U.S. Pat. Nos. 5,510,339 and 5,631,267).

Glucocorticoids are the most useful class of drugs for treating many eosinophil-related disorders. Glucocorticoids, e.g., dexamethasone, methylprednisolone and hydrocortisone produce eosinopenia in normal persons, decrease circulating eosinophils in patients with eosinophilia, and reduce eosinophil influx at inflammatory sites (Butterfield et al., *Anti-inflammatory Steroid Action: Basic and Clinical Aspects*, Schleimer et al., eds., Academic Press, Inc., (1989) at page 151). The mechanism of these effects is still uncertain.

Recently Wallen et al. (*J. Immunol.*, 147, 3940 (1991)) reported the dose-dependent inhibition of IL-5-mediated eosinophil survival by dexamethasone, methylprednisolone and hydrocortisone. Moreover, they disclosed that dexamethasone produced a dose-dependent increase in the $EC_{50}$ for IL-5-mediated viability enhancement. The relative eosinophil viability inhibitory potencies of the glucocorticoids tested correlated with previously described anti-inflammatory potencies and with the affinities of these agents for the glucocorticoid receptor in the following order: dexamethasone>methylprednisolone>hydrocortisone.

For many patients with asthma, glucocorticoids are the principal therapy, and these patients may require chronic high doses of glucocorticoids for months to years. In fact, the disease gradually becomes one of chronic glucocorticoid toxicity, in that the toxicity of these steroids per se can cause severe morbidity and even mortality in the patients. Furthermore, cessation of glucocorticoid therapy leads to withdrawal symptoms, such as malaise and muscle pain. However, presently glucocorticoids are the only effective therapy for severe asthma, and are prescribed long-term despite their toxicity.

A need exists for improved therapeutic methods to treat eosinophil-associated diseases with agents that reduce or inhibit IL-5 activity.

SUMMARY OF THE INVENTION

The present invention provides a therapeutic method comprising counteracting or preventing pathologies mediated by IL-5, including those characterized by eosinophil infiltration, degranulation and inflammation, by the administration of one or more compounds that bind to the eosinophil sulfonylurea receptor, optionally in combination with one or more topical anesthetics and/or glucocorticoids, to an afflicted mammal, e.g., a human. The agents of the invention inhibit or reduce (antagonize) the activity of IL-5 on eosinophils and thus limit or block the pathogenic effects of the proteins secreted and/or released by eosinophils on the tissue of the mammal in need of said treatment.

The present invention further provides a method comprising inhibiting cytokine-induced eosinophil survival or activation by contacting an eosinophil with an effective amount of a sulfonylurea receptor binding agent, optionally in combination with one or more topical anesthetics and/or glucocorticoids. When performed in vitro or in vivo, such a method may be useful for studying the mechanism of action of other therapeutic agents or potential therapeutic agents that effect eosinophil survival or death. Such a method may also be useful to further elucidate the beneficial or pathological effects of eosinophils in biological systems. Additionally, when performed in vivo, such a method may be useful to produce a therapeutic effect.

The present invention also provides a method of treating a disease mediated by IL-5, comprising administering to a mammal afflicted with such a disease, an amount of an agent able to modify (e.g. block) ATP-dependent potassium channels or a protein with which the ATP-dependent potassium channel interacts (such as a SUR), effective to counteract the symptoms of the disease.

The present invention also provides a therapeutic method comprising treating a cytokine (e.g. IL-5) mediated pathology by administering to a mammal (e.g. a human) in need of such therapy, an effective amount of a compound of Formula I, II, VI, or VII as described herein below.

The present method thus provides a treatment for IL-5 mediated pathologies, including bronchial asthma, chronic eosinophilic pneumonia, giant papillary conjunctivitis, vernal conjunctivitis, allergic conjunctivitis, allergic rhinitis, allergic sinusitis, eosinophilic gastroenteritis, allergic gastroenteropathy, atopic dermatitis, bullous pemphigoid, episodic angioedema associated with eosinophilia, and ulcerative colitis.

BRIEF DESCRIPTION OF DRAWINGS

FIG. 12: Shows data that demonstrates the synergistic effects of lidocaine, dexamethasone and glyburide on IL-5 mediated eosinophil survival, as described in Example V (C).

DETAILED DESCRIPTION OF THE INVENTION

Figure 1A:
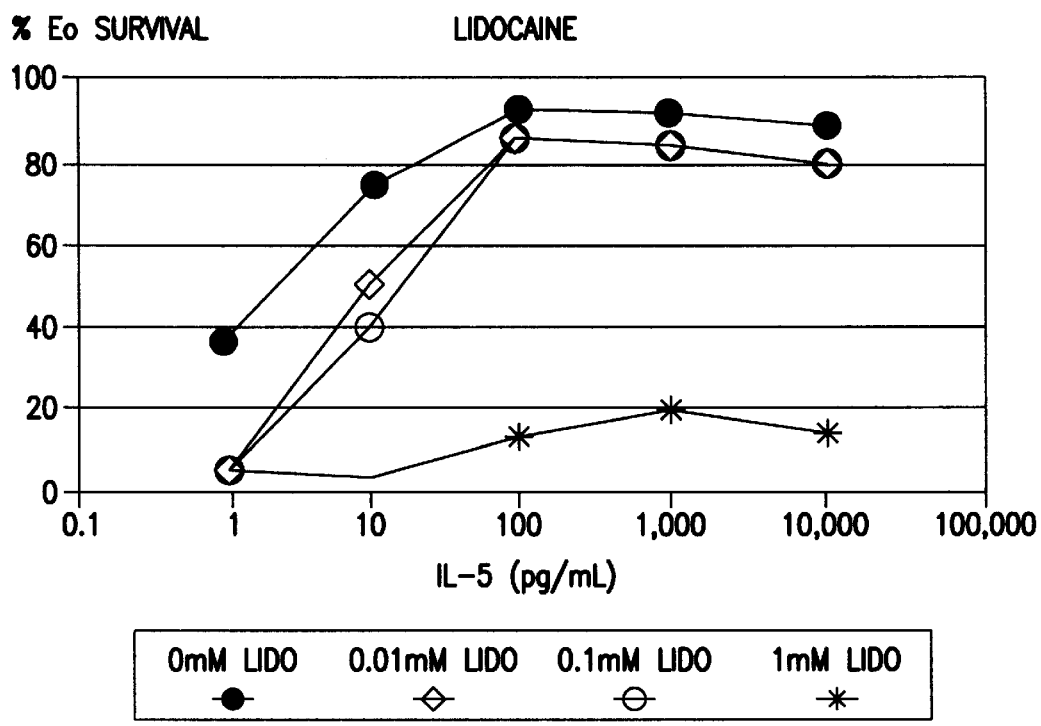
FIG. 1: Inhibition of eosinophil survival mediated by cytokines with lidocaine and glybenclamide (also referred to as glyburide), as described in Example I (B)(2).
Figure 1B:
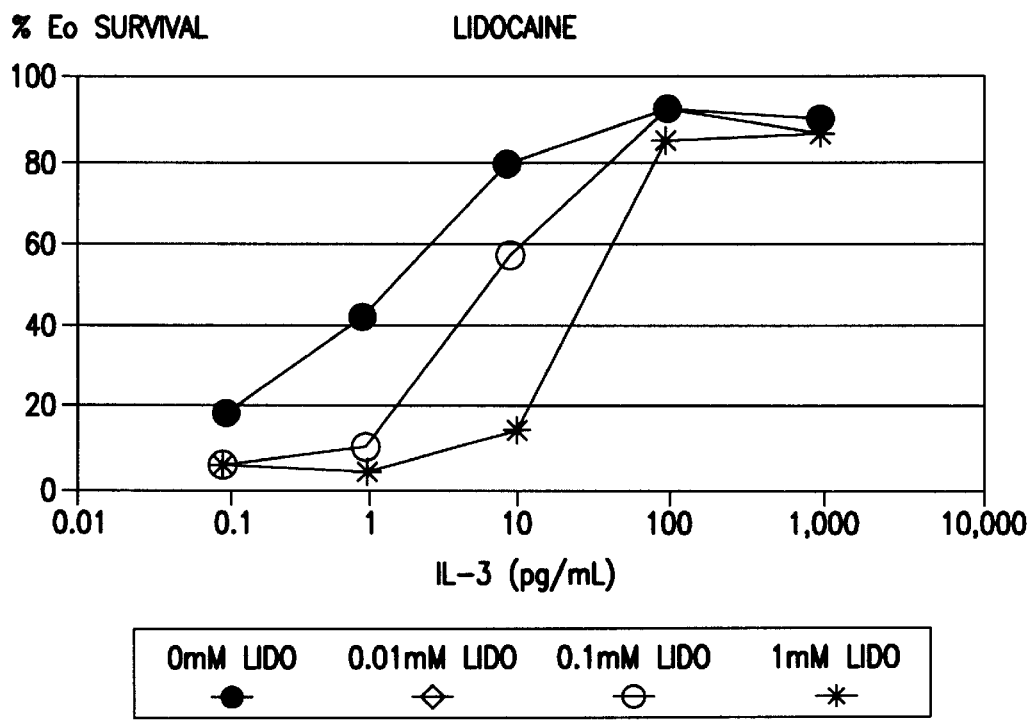
Figure 1C:
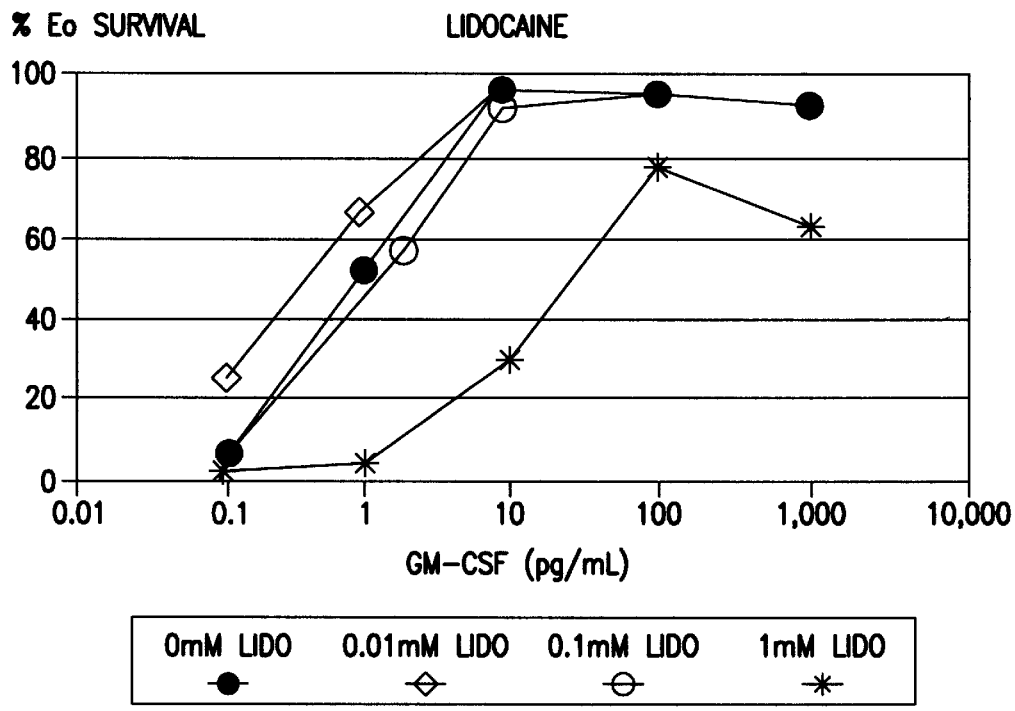
Figure 1D:
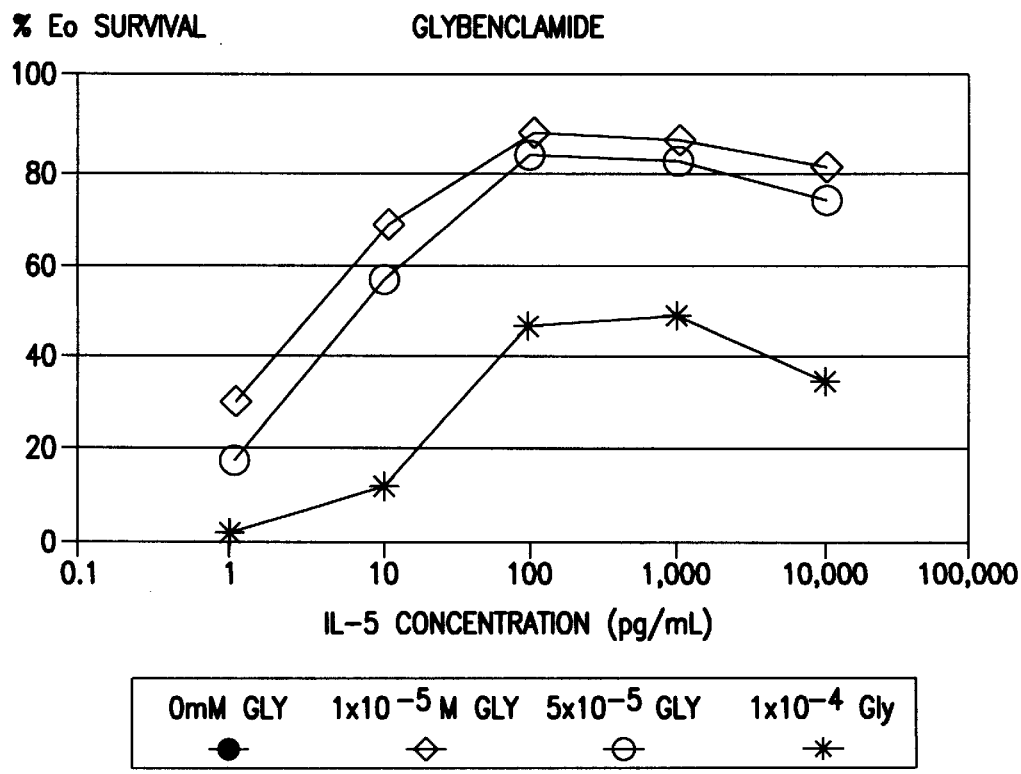
Figure 1E:
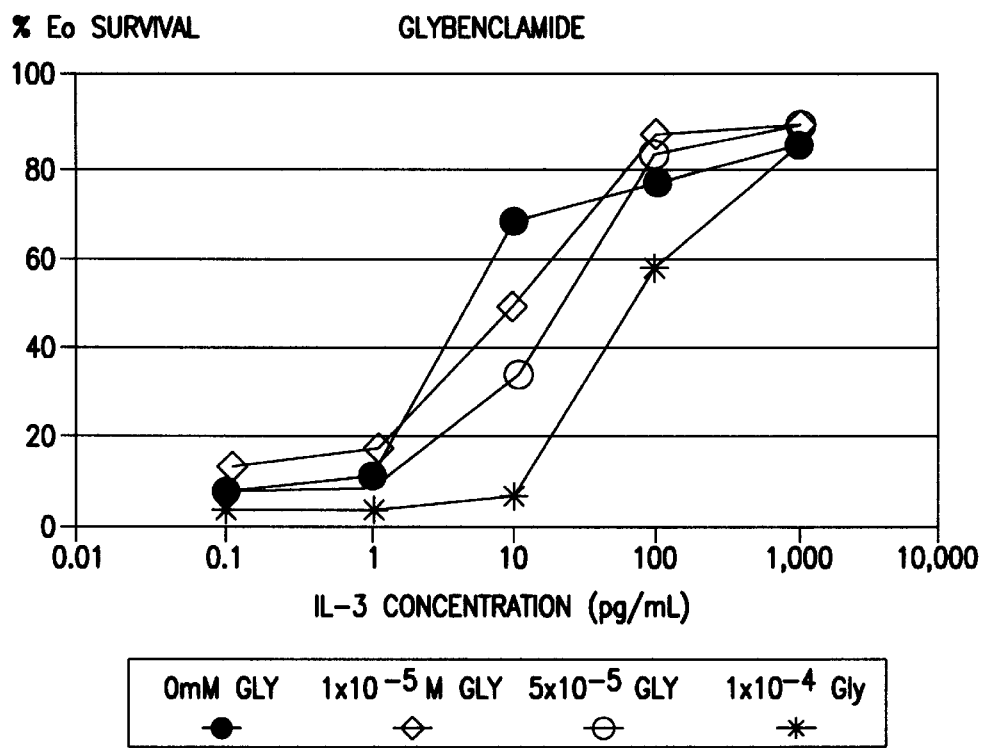
Figure 1F:
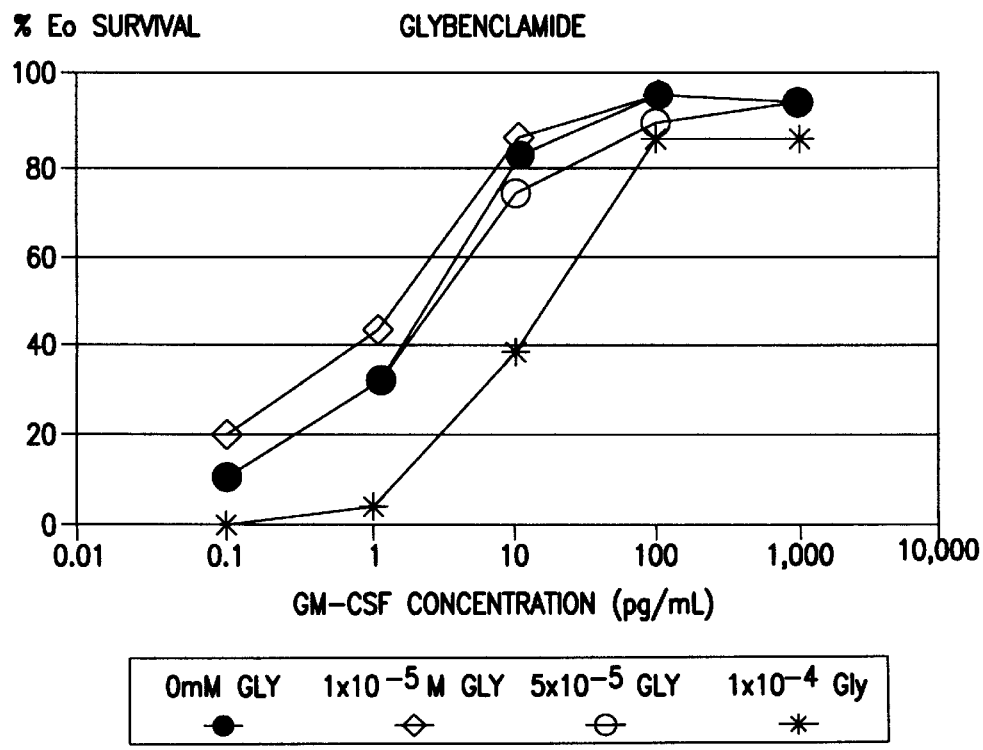
Figure 2A:
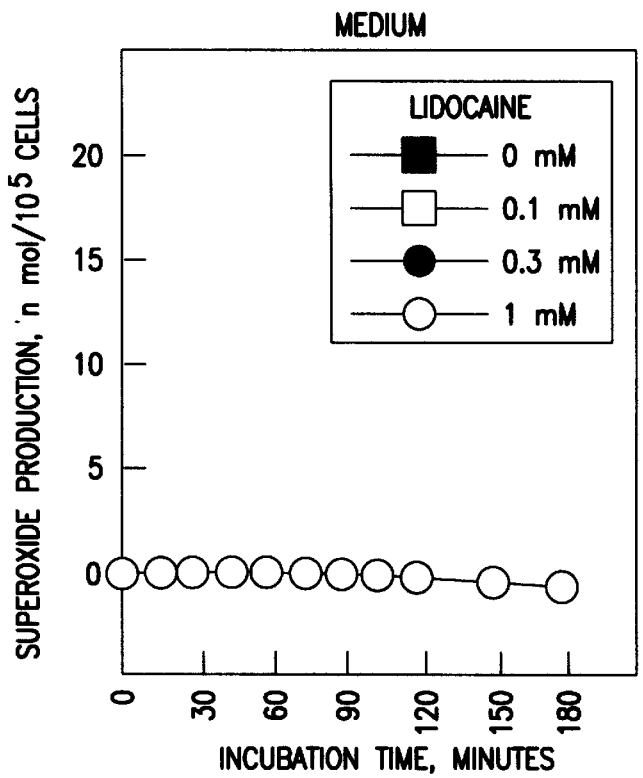
FIG. 2: Eosinophil superoxide production stimulated by cytokines, platelet activating factor (PAF) and immobilized IgG: effect of lidocaine, as described in Example I (B)(2).
Figure 2B:
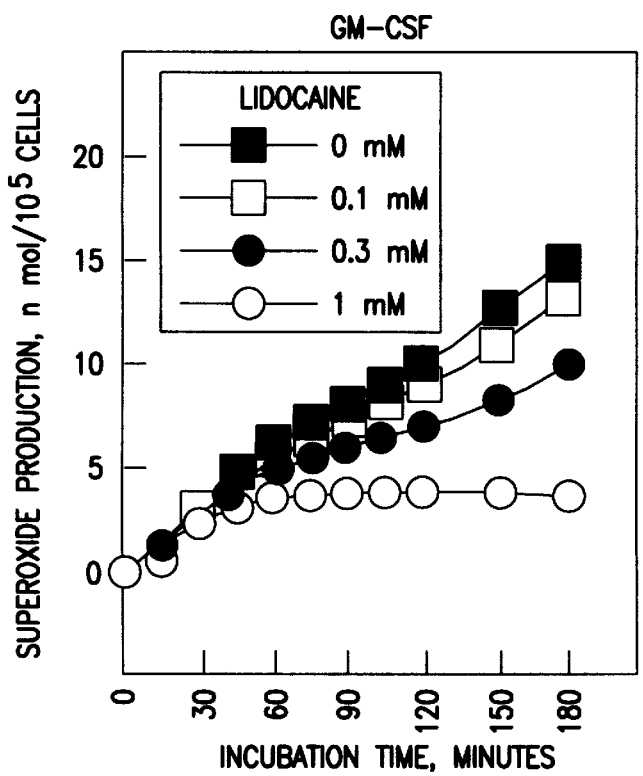
Figure 2C:
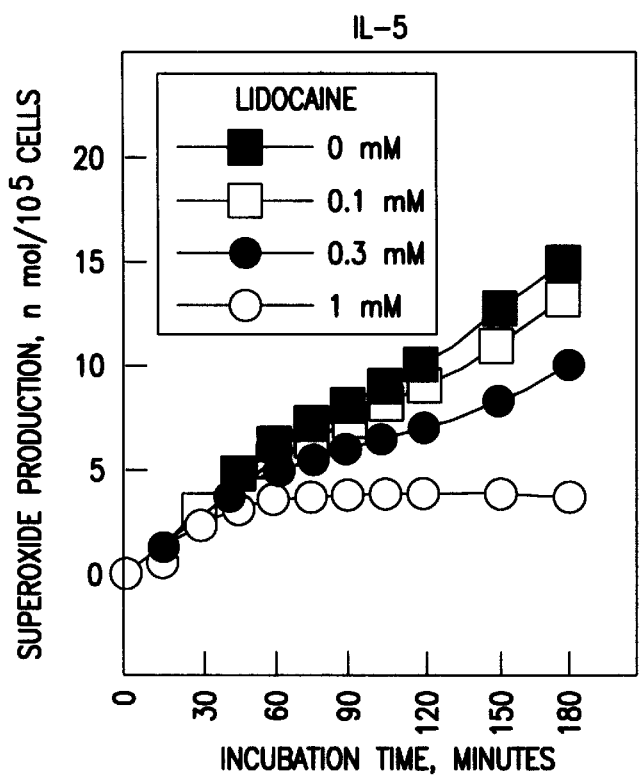
Figure 2D:
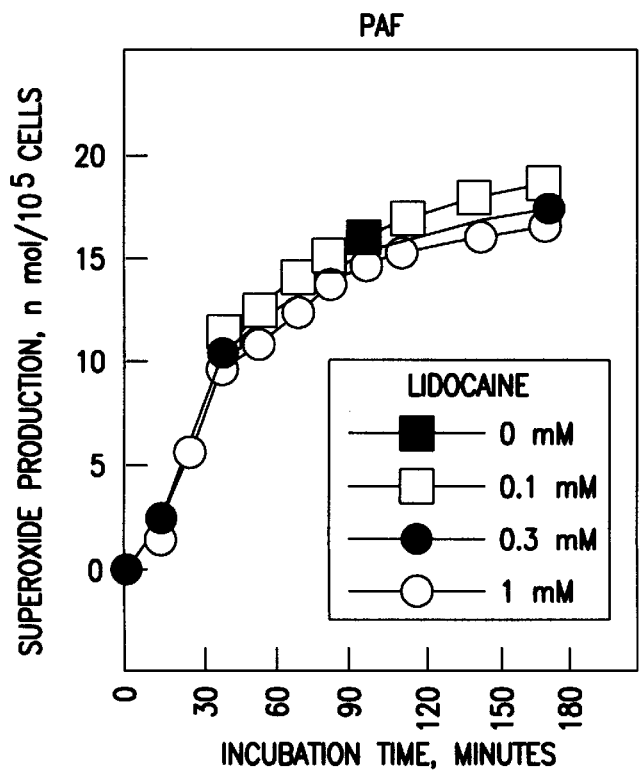
Figure 2E:
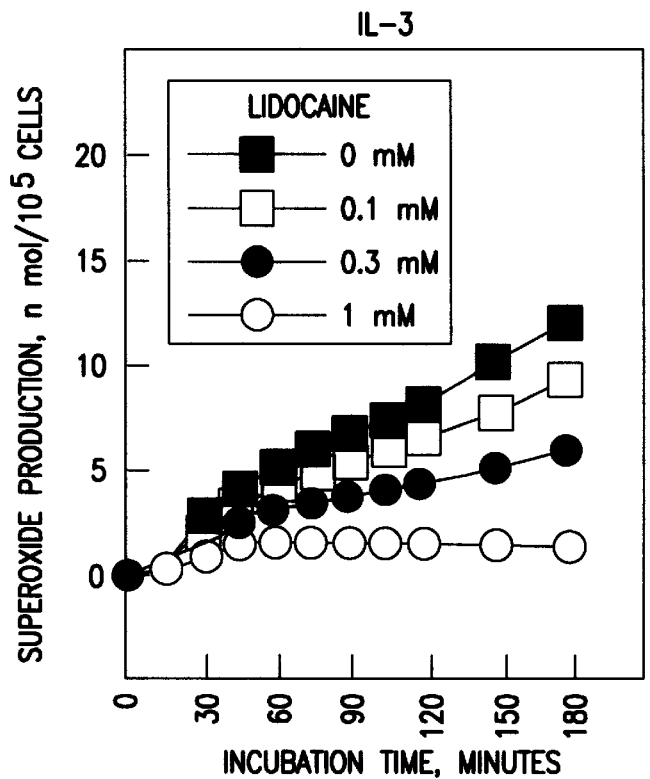
Figure 2F:
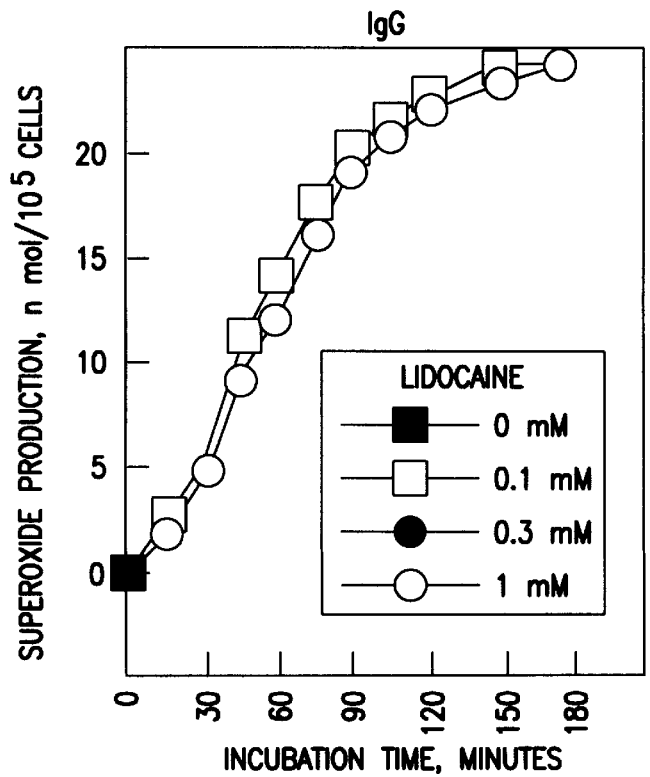

Previously, methods for measurement and localization of eosinophil granule proteins were developed and used for disease investigation, leading to the recognition that the eosinophil likely plays a critical role in pathophysiology. Previous studies have also shown that lidocaine and other topical anesthetics antagonize the action of eosinophil active cytokines.

Sodium channel inhibitors, including tetrodotoxin and amilorides, have been tested for their ability to inhibit the effect of lidocaine on cytokine-mediated eosinophil survival. These experiments were negative, and although tetrodotoxin-insensitive sodium channels do exist, attention was turned to the possibility that a potassium channel might be involved.

A systematic search using known potassium channel inhibitors revealed that glyburide, a second-generation sulfonylurea presently utilized for the treatment of patients with type II diabetes, behaves remarkably similarly to lidocaine. Continuing studies of both of these agents show that they behave very much like glucocorticoids in their ability to inhibit the effect of interleukin IL-3, IL-5, and granulocyte-macrophage colony-stimulating factor (GM-CSF) on eosinophil survival. However, they differ from glucocorticoids in that the activities of both lidocaine and glyburide in this assay are relatively IL-5 specific, i.e. the effects are not reversed fully by increasing concentrations of IL-5. Glyburide had been thought to react with an ATP-sensitive potassium channel ($I_{KATP}$) by interacting with the channel and blocking its function.

New information indicates that $I_{KATP}$ is composed of two subunits. One is a 140 kDa high affinity sulfonylurea receptor (SUR) and the other is an inwardly rectifying potassium channel subunit (Kir6.2). Coexpression of Kir6.2 with SUR reconstitutes the inwardly rectifying potassium channel sensitive to ATP ($I_{KATP}$ (Inagaki, N. et al., Science, 270, 1166 (1995); Sakura, H. et al., FEBS Lett., 377, 338 (1995)). Northern analyses revealed that SUR is expressed only in pancreatic islet tissues, while Kir6.2 is expressed in a variety of tissues, including islet cells (Inagaki, N. et al., Science, 270, 1166 (1995); Sakura, H. et al., FEBS Lett., 377, 338 (1995)). Interestingly, spleen, the only hematopoietic organ tested in these Northern analyses, did not express Kir6.2. SUR confers ATP sensitivity on an ATP-insensitive pore-forming subunit and does not possess intrinsic channel activity, but rather endows sulfonylurea activity on several types of inwardly rectifying K-channels (Ammälä, C. et al., Nature, 379, 545 (1996)). Recent information indicates that the potassium channel and the SUR are separate molecular entities (Aguilar-Bryan, L. et al., Science, 268, 423 (1995)).

Both lidocaine and glyburide inhibit the effects of eosinophil active cytokines in eosinophil survival assays. This finding suggests that these agents may interact with the ATP-sensitive potassium channel ($I_{KATP}$); lidocaine acting upon the inwardly rectifying potassium channel 6.2 (Kir6.2) and glyburide acting upon the SUR.

To test this hypothesis, the activities of lidocaine and glyburide are compared to the activities of glucocorticoids on IL-5 mediated eosinophil functions including superoxide production, degranulation, enhancement of IgG and IgA mediated degranulation, enhanced Mac-1 ($\alpha_M\beta_2$)

expression, increased adhesion, and differentiation of umbilical cord mononuclear cells. To determine whether these agents alter known IL-5 signaling pathways, such as the expression of MAP and Jak-2 kinases, as well as Stat-1α activity, the mechanism of action of lidocaine and glyburide in comparison to dexamethasone is analyzed. The effects of dexamethasone on the transcription factors, NFκB, and its inhibitor, IκBα, are also analyzed and compared to the effects of lidocaine and glyburide.

To determine whether the in vitro effects can be reproduced in an in vivo model, the glucocorticomimetic agents are tested in a murine model of the allergen-induced IgE-mediated late phase reaction. The effects of lidocaine and glyburide on other cells, including basophils and T cells, are tested to determine whether the inhibitory effects observed with the eosinophil response to IL-3, IL-5 and GM-CSF are present.

The present invention also provides a method of treating diseases mediated by the cytokine IL-5, such as parasitic, autoimmune, atopic and malignant diseases, comprising administering to a mammal afflicted with such a disease, such as a human, an amount of an agent able to modify (e.g. block) ATP-dependent K$^+$ channels or a protein with which the ATP-dependent K$^+$ channel interacts, such as the sulfonylurea receptor, and thereby counteract the symptoms of the disease. The agents useful in the present invention are topical anesthetics or a pharmaceutically acceptable salt thereof, and agents which bind to the sulfonylurea receptor. The agents useful in the present invention are believed to act directly or indirectly so as to alter the activity of ATP-dependent K$^+$ channels and/or the sulfonylurea receptor, and counteract the effect of IL-5 on cells which comprise these ATP-dependent K$^+$ channels.

Sulfonylurea Receptor Binding Agents

A number of drugs have been shown to interact with the sulfonylurea receptor (SUR). *Biochemica et Biophysica Acta*, 1175, 45 (1992). Many of these drugs are sulfonylureas, which have the general structure of R$^1$SO$_2$NHCONHR$^2$. Examples of sulfonylureas including glyburide, gliquidone, glibornuride, glipizide, glicazide, chloropropramide, tolbutamide, and tolazamide. Examples of non-sulfonylureas that function like the sulfonylureas in interacting with the SUR are linogliride and meglitinide.

SUR binding agents can be benzoylaminoethyl-substituted benzenesulfonyl-ureas of Formula I:

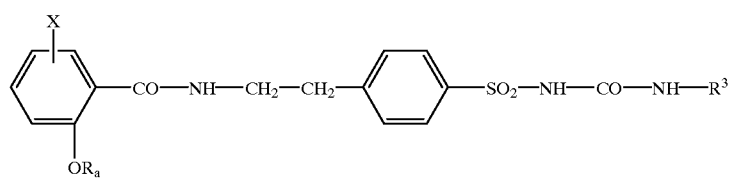

(I)

wherein R$_a$ is lower alkyl or lower alkenyl; X is halogen, preferably chlorine, lower alkyl, preferably methyl, or lower alkoxy, preferably methoxy; and R$^3$ is cyclohexyl, methylcyclohexyl or ethylcyclohexyl, methyl and ethyl being preferably in 4-position of the cyclohexyl radical, norborn-5-en-2-yl or norborn-2-yl.

R$_a$ may represent, for example, methyl, ethyl, propyl, isopropyl, butyl, isobutyl, tert butyl, isoamyl, or allyl. R$^3$ may represent, for example, cyclohexyl, 4-methylcyclohexyl, 4-ethylcyclohexyl, norborn-5-en-2-yl, or norborn-2-yl. One benzenesulfonyl-urea of Formula I is glyburide. These benzenesulfonyl-ureas can be prepared as disclosed in, e.g., U.S. Pat. No. 3,454,635, and they include those disclosed therein.

The SUR binding agents can also be N-phenylsulfonyl-N'-(3-azabicycloalkyl) urea derivatives of Formula II:

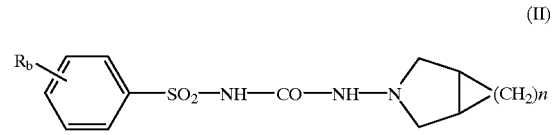

(II)

wherein R$_b$ is a substituent selected from the group consisting of halogen, e.g., chloro, bromo, or fluoro, and a lower-alkyl radical, e.g., methyl, ethyl, propyl, isopropyl, butyl, secondary butyl, tertiary butyl and amyl, and n is 1 to 3 inclusive.

The radical

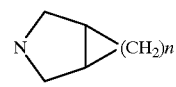

represents an aza-bicyloalkane radical of Formula III, IV or V:

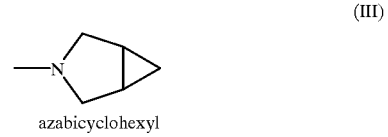

azabicyclohexyl (III)

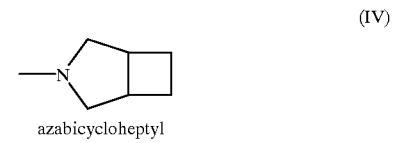

azabicycloheptyl (IV)

-continued

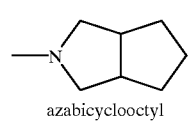

azabicyclooctyl (V)

One such N-phenylsulfonyl-N'-(3-azabicycloalkyl) urea derivative is gliclazide. These derivatives can be prepared as disclosed in, e.g., U.S. Pat. No. 3,501,495 and they include those disclosed U.S. Pat. No. 3,501,495.

The SUR binding agents can also be benzensulfonyl-ureas of Formula VI:

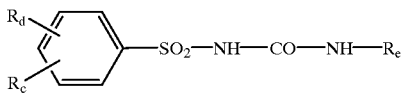

(VI)

wherein $R_c$ is hydrogen, lower alkyl and lower alkoxy; $R_d$ is hydrogen, lower alkyl, lower alkoxy, cycloalkyl and cycloalkyl(lower alkyl); and $R_e$ is lower alkyl, (lower alkenyl), cycloalkyl or cycloalkyl($C_2$–$C_8$)alkyl; and the nontoxic salts thereof.

The radical

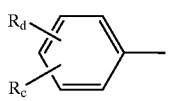

may be, for example, phenyl, methylphenyl, more especially para-methylphenyl, ethylphenyl, propylphenyl, butylphenyl, pentylphenyl or hexylphenyl. The $R_c$ or $R_d$ substituent may preferably be bound in the meta-position or para-position of the phenyl ring. The radical may also be a disubstituted phenyl radical, such as di(lower alkyl)phenyl, di(loweralkoxy)phenyl or (lower alkyl)(lower alkoxy) phenyl.

$R_e$ may be, for example a lower alkyl group, e.g., ethyl, propyl, butyl, pentyl, hexyl, or a lower alkenyl group, e.g., allyl or butylene, a cycloalkyl group, e.g., cyclopentyl, cyclohexyl or cycloheptyl or cycloalkyl(lower alkyl) group, e.g., cyclohexylmethyl or cyclohexylethyl.

One such a benzenesulfonyl-urea is tolbutamide. These benzenesulfonyl-ureas can be prepared by methods disclosed in, e.g., U.S. Pat. No. 2,968,158, and they include the sulfonylureas disclosed therein.

The SUR binding agent can also be a pyrazinyl-carbonamido ethyl derivative of a benzenesulphonyl-urea, such as a compound of Formula VII:

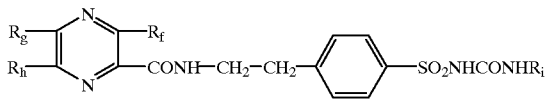

(VII)

wherein $R_f$, $R_g$ and $R_h$ are each independently selected from the group consisting of hydrogen, halogen, lower alkyl, lower alkoxy, hydroxy, amino, acetylamino and phenyl, wherein the lower alkyl, lower alkoxy and phenyl radicals may be substituted by at least one member (e.g 1, 2, or 3) selected from the group consisting of halogen, lower alkyl and lower alkoxy, and $R_i$ is selected from the group consisting of lower alkyl, lower alkenyl, cycloalkyl optionally substituted by lower alkyl or lower alkoxy. $R_f$, $R_g$, and $R_h$ can be, for example, chlorine, fluorine, ethyl, propyl, isopropyl, butyl, isobutyl, ethoxy, propoxy, butoxy or the like. $R_i$ can be, for example, ethyl, propyl, isopropyl, butyl, isobutyl, allyl, cyclopentyl, cyclohexyl, methylcyclohexyl, ethoxycyclohexyl or the like.

A specific SUR binding agent of formula VII useful in the present invention is for example, N-{4-[β-(pyrazine-2-carboxyamido)-ethyl]-benzenesulfonyl}-N'-cyclohexyl-urea; N-{4-[β-(6-methoxy-pyrazine-2-carboxyamido)-ethyl]-benzenesulfonyl}-N'-cyclohexyl-urea; N-{4-[β-(6-chloro-pyrazine-2-carboxyamido)-ethyl]-benzenesulfonyl}-N'-cyclohexyl-urea; N-{4-[β-(5-methyl-pyrazine-2-carboxyamido)-ethyl]-benzenesulfonyl}-N'-cyclohexyl-urea; N-{4-[β-(2,3-dimethyl-pyrazine-5-carboxyamido)-ethyl]-benzenesulfonyl}-N'-cyclohexyl-urea; N-{4-[β-(3-chloro-pyrazine-2-carboxyamido)-ethyl]-benzenesulfonyl}-N'-cyclohexyl-urea; N-{4-[β-(2-chloro-5,6-dimethyl-pyrazine-3-carboxyamido)-ethyl]-benzenesulfonyl}-N'-cyclohexyl-urea; N-{4-[β-(3-methoxy-pyrazine-2-carboxyamido)-ethyl]-benzenesulfonyl}-N'-cyclohexyl-urea; N-{4-[β-(6-methyl-pyrazine-2-carboxyamido)-ethyl]-benzenesulfonyl}-N'-cyclohexyl-urea; or N-{4-[β-(5-methoxy-pyrazine-2-carboxyamido)-ethyl]-benzenesulfonyl}-N'-cyclohexyl-urea.

A prefered SUR binding agent of formula VII is glipizide. The pyrazine derivatives of benzenesulfonyl-ureas can be prepared by methods that are generally known to the art, e.g., U.S. Pat. No. 3,669,966, and include the sulfonylureas disclosed therein.

As used herein, the term "lower alkyl" or "lower alkenyl" or "lower alkoxy" is an alkyl or alkenyl or alkoxy radical containing 1–8 carbon atoms, preferably 1–4 carbon atoms, in a straight or branched chain. As used herein, the term "cycloalkyl" means a ring having 3–8 carbon atoms, and "aryl" is defined as being a ($C_6$–$C_{12}$)aryl (e.g. phenyl or naphthyl).

Topical Anesthetics

Topical anesthetics, all of which are believed to be useful in the present invention, are an art-recognized class of drugs which temporarily interrupt mammalian nerve transmissions. They can generally be grouped into two chemical classifications structurally: the N-arylamides or carboxamides, such as lidocaine; and the aminoalkylbenzoates, such as procaine, benoxinate and proparacaine. Preferred N-arylamides comprise the N-($C_7$–$C_{22}$) arylamides of amino-substituted ($C_1$–$C_5$)carboxylic acids, e.g., N-[(mono- or di-($C_1$–$C_5$)alkyl)phenyl]amides of aliphatic ($C_1$–$C_5$)carboxylic acids, which acids are preferably substituted with the moiety $(R^4)(R^5)N$- wherein $R^4$ and $R^5$ are each H or ($C_1$–$C_5$)alkyl. For example, a preferred carboxylic acid can have the general formula $(R^4)(R^5)N(Y)$ $CO_2H$ wherein $R^4$ and $R^5$ are as defined above and Y is a branched- or straight-chain ($C_1$–$C_5$)alkylene group such as 1,1-ethylene, 1,2-ethylene, methylene, 2,2-propylene, 1,3-propylene, or the like. Another preferred class of N-arylamides are the N-[(mono- or di-($C_1$–$C_4$)alkyl)phenyl] amides of 5- or 6-membered-heterocycloaliphatic carboxylic acids, which acids comprise one or two [($C_1$–$C_4$)alkyl-substituted]N atoms, i.e., N-butylpiperidine-2-carboxylic acid.

The aminoalkylbenzoates include esters between benzoic acids and alcohols of the general formula $(R^6)(R^7)$—N(Y) OH, wherein Y is as defined above, $R^6$ is H or ($C_1$–$C_4$)-alkyl, $R^7$ is ($C_1$–$C_4$)alkyl or $R^6$ and $R^7$ taken together with the nitrogen to which they are attached are a 5- or 6-membered heterocycloaliphatic ring, optionally substituted by ($C_1$–$C_3$) alkyl or comprising an additional ring O- or N-atom. The benzoic acid moiety can be $(R^8)(R^9)ArCO_2H$ wherein Ar is an aromatic —$C_6H_3$— radical or "phenylene" and each $R^8$ and $R^9$ is H, halo, preferably Cl, (($C_1$–$C_4$)alkyl)(H)N—, $H_2N$— or ($C_1$–$C_5$)alkoxy.

Useful topical anesthetics include lidocaine ((2-diethylamino)-N-(2,6-diemethylphenyl)acetamide) (see Lofgren et al. (U.S. Pat. No. 2,441,498), May & Baker (British Patent No. 706409) and J.F. Macfarlane & Co. (British Patent No. 758,224)); bupivacaine (1-butyl-N-(2,6-dimethylphenyl)-2-piperidinecarboxyamide) (see Thuresson et al., (U.S. Pat. No. 2,955,111) and Sterling Drug (British Patent Nos. 1,166,802 and 1,180,712)); mepivacaine (2-piperidinecarboxyamide, N-(2,6-dimethylphenyl)-1-methyl); chloroprocaine (4-amino-2-chlorobenzoic acid 2-(diethylamino)ethyl ester); procaine (4-aminobenzoic acid 2-(diethylamino)ethyl ester); etidocaine (N-(2,6-dimethylphenyl)-2-(ethylpropylamino)butanamide) see, Astra (German Patent No., 2162744); tetracaine (4-(butylamino)benzoic acid 2-(dimethylaminoethyl ester) see Shupe (U.S. Pat. No. 3,272,700); benoxinate (4-amino-3-butoxybenzoic acid 2-(diethylamino)ethyl ester (U.K. Patent No. 654,484)); proparacaine (3-amino-4-propoxybenzoic acid 2-(diethylamino)ethyl ester); dibucaine (3-butoxy-N-[2-(diethylamino)ethyl]-4-quinolinecarboxyamide) see, Miescher (U.S. Pat. No. 1,825,623); dyclonine (1-(4-butoxyphenyl)-3-(1-piperidinyl-1-propanone)); isobucaine (1-propanol, 2-methyl-2-[(2-methylpropyl)amino]benzoate; meprylcaine ([(2-methyl)-(2-propylamino)propyl] benzoate); piperocaine ((2-methylpiperidin-1-ylpropyl (benzoate)); prilocaine (N-(2-methylphenyl)-2-(proplyamino)propanamide); propoxycaine (2-(diethylamino)ethyl-([2'-methyl-4'-amino]benzoate)); pyrrocaine (1-(pyrrolidin-1-yl)-N-(2,6-dimethylphenyl) acetamide; butacaine (((3-dibutylamino)propyl)-(2'-aminobenzoate)); cyclomethylcaine (((3-(2'-methylproperidine-1-yl))propyl)-[4'-cyclohexyloxybenzoate]); dimethyisoquin; diperodon; hexylcaine (([(2-cyclohexylamino)(1-methyl)]ethyl)(benzoate); proparacaine (((2-diethylamino)ethyl) [(4'-propyl-oxyl-3'-amino)benzoate]); cocaine and its analogs (see, F. I. Carroll et al., *J. Med. Chem.*, 34, 2719 (1991); *Eur. J. Pharmacol.*, 184, 329 (1990); and the pharmaceutically acceptable salts thereof.

Preferred salts of SUR receptor binding agents e.g., the sulfonylureas (such as for example compounds of formulae I, II, VI and VII), and of the topical anesthetics include the nontoxic amine addition salts of inorganic and organic acids, e.g., the hydrochloride, hydrobromide, sulfate, oxalate, fumarate, citrate, malate, propionate and phosphate salts. The hydrochloride and sulfate salts are preferred for use in the present invention.

These topical anesthetics and the salts thereof are discussed in detail in *Remington's Pharmaceutical Sciences*, A. Osol, ed., Mack Pub. Co., Easton, Pa. (16th ed. 1980), and in *The Merck Index* (11th ed. 1989).

Administration and Dosages

While it is possible that for use in therapy the SUR binding agent, optionally in combination with a topical anesthetic and/or glucocorticoid (the "active agent") or their salts may be administered as the pure dry chemicals, as by inhalation of a fine powder via an insufflator, it is preferable to present the active ingredient as a pharmaceutical formulation. The invention provides a pharmaceutical formulation comprising one or more active agent, or pharmaceutically acceptable salts thereof, together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The formulations may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

Pharmaceutical formulations suitable for oral administration may be presented as discrete unit dosage forms such as hard or soft gelatin capsules, cachets or tablets each containing a predetermined amount of the active ingredient; as a powder or as granules; as a solution, a suspension or as an emulsion; or in a chewable base such as a synthetic resin or chicle. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g., by injection, for example, bolus injection or continuous infusion) and may be presented in unit dose form in ampules, pre-filled syringes, small volume infusion containers or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in A. Fisher et al. (U.S. Pat. No. 4,788,603), or R. Bawa et al. (U.S. Pat. Nos. 4,931,279; 4,668,506 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122; 4,383,529; or 4,051,842.

When desired, the above-described formulations can be adapted to give sustained release of the active ingredient employed, e.g., by combination with certain hydrophilic polymer matrices, e.g., comprising natural gels, synthetic polymer gels or mixtures thereof.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing, in addition to the active ingredient, such carriers as are known in the art to be appropriate.

Pharmaceutical formulations include those suitable for administration by inhalation or insufflation or for nasal, intraocular or other topical (including buccal and sublingual) administration. The formulations may, where appropriate, be conveniently presented in discrete dosage units and may be prepared by any of the methods well known in the art of pharmacy. All methods include the step of bringing into association the active compound with liquid carriers or finely divided solid carriers or both.

For administration to the upper (nasal) or lower respiratory tract by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the active agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the active agent may be administered via nose drops, a liquid spray, such as via a plastic bottle atomizer or metered-dose inhaler. Typical of atomizers are the Mistometer (Wintrop) and the Medihaler (Riker).

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

Formulations suitable for topical administration in the mouth or throat include lozenges comprising active agent in a flavored base, usually sucrose and acacia or tragacanth; pastille comprising the active agent in an inert base such as gelatin and glycerin or sucrose and acacia; and mouthwashes comprising the active agent in a suitable liquid carrier.

The pharmaceutical compositions according to the invention may also contain other active ingredients such as antimicrobial agents, or preservatives. The active agent may also be used in combination with other therapeutic agents, for example, bronchodilators or anti-inflammatory agents.

It will be further appreciated that the amount of the active agent required for use in treatment will vary not only with the particular compound selected but also with the route of administration, the nature of the condition being treated and the age and condition of the patient and will be ultimately at the discretion of the attendant physician or veterinarian. In general, however, a suitable unit dose for counteracting respiratory tract symptomatology will deliver per day from about 0.02 to about 10–15 mg/kg, e.g., from about 0.10 to about 5.0 mg/kg of body weight of the SUR binding agent, along with up to an equal dose of topical anesthetic.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The desired dose may conveniently be presented in a single dose or as divided doses administered at appropriate intervals, for example, as two-, three-, four or more sub-doses per day. The sub-dose itself may be further divided, e.g. into a number of discrete loosely spaced administrations; such as multiple inhalations from an insufflator or by application of a plurality of drops into the eye or nose.

The invention will be further described by reference to the following detailed examples.

EXAMPLE I

Analyses of Cytokines in the Body Fluids of Individuals with Eosinophilia

A. Analysis of Eosinophils from Human Peripheral Blood

1. Eosinophil Purification from Human Peripheral Blood

Eosinophils were purified from human peripheral blood, as previously described by T. Fujisawa et al., *J. Immunol.*, 144, 642 (1990). Briefly, heparinized (10 U/ml) venous blood was obtained from normal volunteers or patients with mild asthma or hay fever and sedimented with 6% dextran in 0.9% NaCl (Gentran 70) (Travenol Laboratories, Deerfield, Ill.) at 5:1 (v/v) ratio for 45 minutes at 37° C. The buffer coat was collected and washed twice in Pipes buffer (25 mM piperazine-N, N'-bis-[2-ethanesulfonic acid]), 110 mM NaCl, 5 mM KCl, 25 mM NaOH, 5.4 mM glucose, pH 7.4) with 50 U/ml DNase (Sigma Chemical Co., St. Louis, Mo.). The cells were suspended in 2.4 ml of Percoll (Sigma), density 1.070 g/ml, with 5% heat-inactivated defined calf serum (DCS) (Hyclone Laboratories, Logan, Utah) and overlayered on a discontinuous Percoll gradient consisting of the following densities (g/ml): 1.080, 1.085, 1.090, 1.100, and 1.120. The osmolarity of Percoll ranged from 290 to 315 mOsm/kg and the pH was 7.4. Cells were centrifugated through the gradient at 1,500 g in a JA-20 fixed angle rotor on a Beckman J2-21 centrifuge at 4° C. for 45 minutes. Fractions were collected and eosinophil numbers were determined utilizing Randolph's stain. Eosinophil-rich fractions were pooled, washed twice in Pipes buffer with 1% DCS, and used for experiments immediately. The eosinophil preparations were >80% pure and >98% viable, as determined by Randolph's stain and by trypan blue exclusion, respectively. The contaminating cells were neutrophils. There was no contamination by lymphocytes or monocytes.

2. Eosinophil Survival Assay

Eosinophils were cultured at 37° C. and 5% $CO_2$ in 200 µl Hydri-Care medium containing gentamicin and 10% DCS in 90-well, flat-bottom tissue culture plates at a cell concentration of $2.5 \times 10^5$/ml or $1.25 \times 10^5$ cells/ml. No difference in viability was observed at these two cell concentrations. Viability was determined at day 4 for all experiments unless otherwise specified. A Neubauer hemacytometer (C. A. Hausser & Son; Philadelphia, Pa.) and fluorescence microscopy were used to count live cells, stained green with fluorescein diacetate (B. Rotman et al., *PNAS USA*, 55, 134 (1966)), and dead cells, stained red with propidium iodide (G. R. Pullen et al., *J. Immunol. Methods*, 43, 87 (1981)). Viability was calculated by the formula: viability, %=(live cells)/(live cells+dead cells))×100%. Each experiment was performed in duplicate and all results represent three or more experiments.

3. Cytokine-mediated Eosinophil Survival and Effects of Topical Anesthetics

As reported by N. Wallen et al., *J. Immunol.*, 147, 3940 (1991), the responses of eosinophil survival to increasing concentrations of IL-5, IL-3, GM-CSF and IFN-γ were determined. For determination of the effect of lidocaine and other topical anesthetics on cytokine-mediated survival, eosinophils were cultured in the presence of specified cytokine and topical anesthetic concentrations, and viability in the presence of the test anesthetic was compared to viability in cytokine-enriched medium alone. Anesthetics were dissolved in 0.15 M NaCl, stored at −20° C., and diluted in medium just before use; thus, 0.15 M NaCl was used as a control for each experiment. The effects of the anesthetics and the vehicle control on cytokine-mediated viability were tested. Inhibition of viability was determined by the formula: inhibition, $\% = (V_{med} - V_{an})/V_{med} \times 100\%$, where $V_{med}$ = viability in cytokine-enriched medium alone and $V_{an}$ = viability at the specified anesthetic and cytokine concentrations. $IC_{50}$ is the concentration of anesthetic that produces 50% inhibition of viability. The change in dose-response to cytokine in the presence of varied lidocaine concentrations was tested and the $EC_{50}$ is for each lidocaine concentration was calculated. $EC_{50}$ is the IL-5 concentration that produces 50% enhancement of viability; the 50% viability enhancement was determined by subtracting the baseline viability from the maximum viability and dividing the difference by two, or $V_{50} = (V_{max} - V_{min})/2 + V_{min}$, where $V_{max}$ = viability in the absence of cytokine and anesthetic. For determination of the time course of the anesthetic effect, the medium was supplemented with rIL-5, 220 fM, or 890 fM, and the effects of anesthetic 1000 nM, 100 nM, or control were tested by comparing viability at 1, 2, and 4 days in the presence or absence of anesthetic.

4. Statistics

All values are expressed at the mean ± SEM and represent three or more experiments performed in duplicate. Significance of differences in viability were determined using a one-tailed Student's t-test.

5. Results

To measure eosinophil active cytokines, an eosinophil survival assay was established (H. Kita et al., *J. Exp. Med.*, 174, 745 (1991)). This assay showed that two cytokines, namely IL-3 and GM-CSF, were produced by eosinophils themselves when the eosinophils were stimulated with ionomycin and phorbol myristate acetate. To determine whether an eosinophil active cytokine(s) was elevated in eosinophil-associated diseases, the level of IL-5 in patients with episodic angioedema associated with eosinophilia was measured.

Elevated serum IL-5 levels were readily detected by immunoenzymetric assay, and blood eosinophil levels and serum IL-5 levels fluctuated in concert. IL-5 levels were increased in patients receiving IL-2 for therapy of malignant disease, and again blood eosinophil levels and serum IL-5 levels fluctuated in concert. IL-2 administration caused a marked increased in peripheral blood eosinophils and a syndrome characterized by fluid retention and weight gain (referred to as a capillary leak syndrome). Clinically, this syndrome is remarkably similar to episodic angioedema.

Furthermore, eosinophil granule proteins are deposited in the dermis of patients with both episodic angioedema as well as in the IL-2 capillary leak syndrome. Recent observations showed that eosinophil granule proteins increase microvascular macromolecule transport. For example, MBP, ECP and EPO, in the nm range, and EDN, in the μm range, produce clear-cut increases in vascular permeability.

B. Analysis of Eosinophils from Bronchoalveolar Lavage Fluids

Eosinophils are prominent in the airways of patients with asthma. Also, cytokines may be critical for localization of eosinophils to sites of inflammation in the airways of asthma patients. Therefore, cytokines produced during allergen-induced eosinophil-associated inflammation after pulmonary segmental antigen challenge were analyzed.

1. Pulmonary Inflammation from Antigen Challenge

In bronchoalveolar lavage (BAL) fluids obtained 20 minutes after antigen challenge in patients with ragweed pollen allergic rhinitis, the levels of tryptase, histamine and leukotriene $(LT)C_4$ increased. There were no increases in the levels in normal volunteers. The numbers of inflammatory cells did not increase in either group. BAL fluids from the late phase reaction at 48 hours showed marked increases in the numbers of eosinophils in an allergen dose-related manner, showed increases in the concentrations of all four eosinophil granule proteins in a dose-related manner, and a clear-cut increase in the concentrations of IL-5, as measured by an immunoradiometric assay. Correlation matrices showed positive relationships between IL-5 and eosinophils ($r_S$=+0.84), between IL-5 and eosinophil granule proteins including MBP, EPO and ECP ($r_S$ ranging from +0.79 to +0.87) and, finally, between IL-5 and $LTC_4$ ($r_S$=+0.81) (all significant at p<0.001).

Subsequently, BAL fluids from this study were tested for cytokines using the eosinophil survival assay. A dose-response relationship was shown between eosinophil survival enhancing activity and the doses of the antigen challenge. As expected in the BAL fluids, the degree of eosinophil degranulation correlated with cytokines. Overall, the eosinophil survival activity in the late inflammatory lesions following segmental bronchoprovocation with allergen is mainly associated with IL-5 with contributions from GM-CSF.

In addition, patients undergoing late phase reactions in the lung had increased vascular permeability in BAL fluids, as judged by increases in BAL fluid albumin. These increases in vascular permeability strongly correlated with the levels of BAL eosinophils, r=+0.82 (p<0.001) and with the levels of EDN in the BAL fluids, r=+0.88 (p<0.001). Overall, eosinophil recruitment and degranulation are associated with large increases in bronchovascular permeability after segmental antigen challenge. These results are consistent with the eosinophil granule proteins' potential to increase vascular permeability. In addition, eosinophil survival activity in BAL fluids, identified as IL-5 by neutralization with monoclonal antibodies (mAb), was positively and significantly correlated both with the levels of eosinophil granule proteins and with the albumin concentrations. Thus, IL-5 correlates with eosinophil recruitment, eosinophil degranulation, and lung injury, and IL-5 is likely a critical determinant of inflammation in the lung 24 hours after antigen challenge.

2. Spontaneous Pulmonary Inflammation

To test whether the model of pulmonary inflammation described above could be applied to spontaneous inflammation in patients with asthma, levels of IL-5 protein in the BAL fluids of spontaneously symptomatic patients with asthma were investigated. BAL fluids were obtained from patients hospitalized for treatment of bronchial asthma who underwent BAL as a therapeutic procedure. These BAL fluids were compared to BAL fluids from asymptomatic patients with asthma. The results showed that the percentages of BAL eosinophils (10.5% vs. 0.6%) (p=0.0001) and EDN levels (385 ng/ml vs. 6.3 ng/ml) (p=0.0001) were greater in BAL fluids derived from symptomatic compared to asymptomatic asthmatics. Furthermore, IL-5 levels measured by immunoradiometric assay were significantly higher in symptomatic compared to asymptomatic asthmatics (274 pg/ml vs.<13 pg/ml) (p=0.02). Strikingly, increased IL-5 levels were noted in symptomatic asthmatics with BAL absolute eosinophil counts greater than $1\times10^6$ (IL-5, 664 pg/ml) compared to symptomatic asthmatics with BAL eosinophil counts <$1\times10^6$ (IL-5, <13 pg/ml) (p=0.005). Thus, IL-5 is not only induced in the experimental models of allergen-induced asthma, but it can also be detected as asthma progresses from the asymptomatic to the clinically symptomatic state in patients with significant BAL eosinophilia.

The above results used an immuoenzymetric assay to measure IL-5 (S. Sur et al., *J. Allergy Clin. Immunol.*, 96, 661 (1995)). This assay was used because earlier experiments found an inhibitor of eosinophil survival in BAL fluids from patients underlying BAL as a therapy for asthma (Ohnishi et al., supra). BAL fluids from 40 symptomatic asthma patients showed that in 15 patients eosinophil survival activity was detectable. Surprisingly, in the remaining 25 patients, spontaneous survival of eosinophils in the assay was decreased. Investigation of the inhibitory factor tested whether glucocorticoids administered intravenously to patients before BAL treatment caused a diminution in eosinophil survival.

An earlier study had analyzed the effect of glucocorticoids on cytokine-induced survival of human eosinophils in vitro. It showed that eosinophil active cytokines including IL-3, IL-5, GM-CSF and interferon (IFN)-γ enhanced eosinophil survival in a dose-dependent manner. When eosinophils were cultured with a submaximal concentration of IL-5 (220 fM), dexamethasone, methyl prednisolone and hydrocortisone inhibited eosinophil survival in a dose-dependent manner. In contrast, estradiol and testosterone (1,000 nM) had no effect on eosinophil survival. When eosinophils were incubated with varying concentrations of human recombinant IL-5 (rIL-5) and 1,000 nM dexamethasone, survival inhibition was reduced at higher concentrations of rIL-5. Similarly, IL-3 and GM-CSF reversed the effects of 1,000 nM dexamethasone. However, even 1,000 U/ml IFN-γ did not overcome the dexamethasone inhibition, indicating a difference between eosinophil survival induced by IFN-γ and these other cytokines. Thus, glucocorticoids exert a direct, inhibitory effect on eosinophil survival, and high doses of cytokines overcome glucocorticoids.

The BAL fluids that inhibited eosinophil survival were also analyzed for glucocorticoids. However, glucocorticoids could not be identified with high performance liquid chromatography, and the possibility of another inhibitor was entertained. The inhibitory activity in the BAL fluids was of low molecular weight (<3,000), and it resisted heating at 100° C. for 30 minutes. Further, the inhibitory substance was not toxic for eosinophils, and its activity mimicked that of glucocorticoids in that it was overcome by high concentrations of IL-5, IL-3 and GM-CSF, but not by IFN-γ.

Because lidocaine is used as a topical anesthetic in performance of BAL, it was tested as a potential cytokine inhibitor. Indeed, lidocaine at a concentration of 0.25 mg/ml inhibited IL-5 mediated eosinophil survival, and the pattern of inhibition of IL-5 activity was essentially identical to glucocorticoids, i.e., high concentrations of IL-3, IL-5 and GM-CSF overcame the lidocaine inhibition, whereas high concentrations of IFN-γ did not. Furthermore, lidocaine inhibited IL-5 mediated survival in a dose-related manner and was about 30-fold less potent than dexamethasone.

Finally, the concentrations of lidocaine measured in the inhibitory BAL fluids were strongly correlated ($r_s$=+0.9; p=0.04; n=5) with the ability of the BAL fluid to inhibit eosinophil survival. These results suggested that lidocaine was the inhibitory factor in the BAL fluids and that it behaved in a manner surprisingly similar to glucocorticoids.

Because lidocaine was glucocorticomimetic in the eosinophil survival assay, its anti-inflammatory activities in asthma was tested. Twenty patients with severe glucocorticoid-dependent asthma suffering from side effects of exogenous hypercortisolism were treated with inhaled lidocaine. Thirteen of these 20 patients were able to discontinue oral glucocorticoids entirely, in spite of prior glucocorticoid dependence; four reduced their daily glucocorticoid requirement by 80–90% while controlling asthma symptoms. Three patients had no apparent response, had continued severe asthma symptoms and were not able to reduce glucocorticoids.

The mechanism by which lidocaine interferes with eosinophil active cytokine function was explored by determining whether tetrodotoxin and amiloride derivatives interfered with lidocaine activity. However, neither of these had any effect. To determine whether lidocaine might be altering a potassium channel, a series of potassium channel blockers revealed that glyburide, a drug used for treatment of type II diabetes which had been used to define $I_{KATP}$ and now is recognized to interact with the sulfonylurea receptor (SUR) on β islet cells of the pancreas, behaved remarkably similarly to lidocaine.

To test the inhibition of cytokine-mediated eosinophil survival by lidocaine and glybenclamide (also referred to as glyburide), purified eosinophils were tested in an eosinophil survival assay for four days and their viability determined by staining with propidium iodide and analysis by FACScan flow cytometry and PC Lysys software (Becton Dickinson Immunocytometry Systems, San Jose, Calif.). FIG. 1 shows the results of this experiment. In FIG. 1, titrations of glyburide ("glybenclamide") are compared with lidocaine for their effects on eosinophil survival stimulated by IL-5, IL-3 and GM-CSF. FIG. 1 shows both glyburide and lidocaine had preferential activity on IL-5. Both lidocaine and glyburide shift the dose-response curve for the quantities of IL-3 and GM-CSF needed to maintain eosinophil survival to the right. For example, in the case of GM-CSF, the quantities needed for 50% survival of cells changed from ~0.5 pg/ml in the absence of lidocaine to ~50 pg/ml in the presence of 1 mM lidocaine. Similar results were seen with glyburide.

Surprisingly, the inhibitory effects of lidocaine and glyburide on IL-5 mediated survival were not overcome by increased concentrations of IL-5; the failure of IL-5 to overcome the effects of these drugs stands in sharp contrast to the effects of glucocorticoids on IL-5 mediated eosinophil survival, where increased concentrations of IL-5 completely overcame the effects of 1 μM of dexamethasone.

To test the effect of lidocaine on eosinophil superoxide production stimulated by cytokines, platelet activating factor (PAF) and immobilized IgG, purified eosinophils were stimulated with IL-5, IL-3 and GM-CSF, all at 10 ng/ml, 1 μM PAF and exposed to plates coated with immobilized IgG. The cells were incubated for up to 3 hr at 37° C. and superoxide production was analyzed. FIG. 2 shows the results of this experiment. Lidocaine inhibited IL-5, IL-3 and GM-CSF stimulated superoxide production in a dose-related manner. In contrast to the results with eosinophil survival, the effect on this eosinophil finction was approximately equal among the three cytokine agonists. In contrast, the ability of platelet-activating factor (PAF) and IgG complexes to stimulated eosinophil superoxide production was not affected by lidocaine. Thus, lidocaine does not non-specifically alter eosinophil functioning, but rather has a specific effect on cytokine mediated stimulation.

EXAMPLE II

Lidocaine and Sulfonylureas as Glucocorticomimetic Agents

Glucocorticoids block the enhanced eosinophil survival stimulated by IL-3, IL-5, GM-CSF and IFN-γ (Wallen, N., et al., *J. Immunol.*, 147, 3490, (1991)). The inhibitory effects of glucocorticoids were overcome by increased concentrations of IL-3, IL-5, GM-CSF, but not IFN-γ. Moreover, a factor in bronchoalveolar lavage (BAL) fluid inhibits eosinophil survival in a manner similar to that described for glucocorticoids. Analyses of this factor revealed that it is lidocaine (used for topical anesthesia during the bronchoscopy). Lidocaine inhibited IL-5 mediated eosinophil survival in vitro at ~10–100 µM.

An open clinical trial of nebulized lidocaine showed that 17 of 20 patients with severe glucocorticoid-dependent asthma suffering from the side effects of exogenous hypercortisolism were benefited. Thirteen of the 17 discontinued oral glucocorticoids entirely, despite lengthy glucocorticoid dependence (mean 6.6 years and median 3.0 years for the 20 patients); 4 achieved reduction in daily glucocorticoid requirement by 80–90% while maintaining symptom control (duration of glucocorticoid dependence for responders, mean 6.2 years and median 3.2 years). Thus, lidocaine may be a useful therapy for chronic asthma, permitting reduction or elimination of oral glucocorticoid therapy.

To determine the mechanism by which lidocaine exerts its glucocorticomimetic effect, sodium and then potassium channel blockers were analyzed. These studies showed that glyburide, an inhibitor of the ATP-sensitive potassium channel, produces effects on eosinophil survival essentially identical to lidocaine. It is now recognized that the sulfonylurea receptor (SUR) and the potassium channel, Kir6.2, although finctionally interrelated, are separate molecular entities. Therefore, the above information suggests that the survival-promoting activity of IL-5 on eosinophils is mediated, in part, through $I_{KATP}$ composed of both the potassium channel and the SUR. However, whether glyburide acts on the same high affinity receptor in eosinophils as is present in the pancreatic islet β cell is not clear. Both high and low affinity SUR exist (Ashcroft, S. J. H., Ashcroft, F. M. *Biochim. Biophys. Acta*, 1175, 45, (1992)), but little is known about the low affinity receptors. The concentration of glyburide needed for its maximum effect is ~100 µM and, thus, greater than that expected for the pancreatic islet β cell high affinity SUR. Prior work with photoaffinity labeling on the β-islet cell SUR showed the presence of proteins of ~38–45 and 65 kDa in addition to high affinity 140 kDa SUR (Aguilar-Bryan, et al., *J. Biol. Chem.*, 265, 8218 (1990)); Schwanstecher, M., et al., *J. Biol. Chem.*, 269, 17768 (1994)). Because the 140 kDa SUR constitutes the high affinity receptor, these other proteins may be ancillary molecules or they may form another SUR.

These studies support the existence of two glucocorticomimetic agents, namely lidocaine and glyburide. The evidence that lidocaine appears to benefit patients with glucocorticoid-dependent asthma indicates that the glucocorticomimetic agents can be useful therapeutically. To test whether glyburide interacts with the high affinity SUR receptor and whether lidocaine interacts with the potassium channel, and to determine whether these agents interrupt IL-5 signaling pathways, or mimic the effects of glucocorticoids on IcBa, the following experiments were conducted.

To test the activities of lidocaine and glyburide, in comparison to glucocorticoids, on IL-5 stimulated eosinophil functions, the following measures of eosinophil function are employed: 1) superoxide production, 2) degranulation, 3) enhancement of IgG and sIgA mediated degranulation, 4) increased Mac-1 ($\alpha_M\beta_2$) expression, 5) increased adhesion, and 6) differentiation of umbilical cord blood mononuclear cells to eosinophils. Thus, the IL-5 stimulated functions blocked by glucocorticoids, and whether these functions are blocked by lidocaine and/or glyburide, is determined.

The mechanism(s) by which glucocorticoids, lidocaine and glyburide act on eosinophils is analyzed by comparing their effects on IL-5 signal transduction pathways, and on IκBα. The presence of the SUR and Kir6.2, the recently cloned inward-rectifier potassium channel, on eosinophils is determined by FACS using a fluorescent glyburide derivative, by Scatchard analyses using radiolabeled glyburide, by RT-PCR for expression of the 140 kDa SUR and for expression of Kir6.2, and by patch clamp analyses. Assuming that a SUR is present, the peptides composing the SUR are analyzed by photoaffinity labeling employing 5-iodo-2-hydroxy-glyburide, which covalently binds to membrane proteins. Using this approach, polypeptides composing the SUR are analyzed to obtain molecular weights and amino acid sequence. Immunization and challenge of BALB/c mice with ragweed pollen extracts to stimulate an IL-5-mediated peritoneal eosinophilia can serve as a model of an allergen-mediated late phase reaction. This animal model is used to compare the effects of glucocorticoids and the glucocorticomimetic agents, lidocaine and glyburide, on eosinophil infiltration and degranulation. The effects of glyburide and lidocaine in comparison to glucocorticoids is analyzed on the stimulation of other cells by cytokines, including IL-3, IL-5 and GM-CSF as well as IL-2 and IL-4. For example, IL-3, IL-5 and GM-CSF markedly enhance histamine release by human basophils, and IL-2 and IL-4 stimulate proliferation of human T cells.

A. Purification of Eosinophils by CD16 Negative Selection

Eosinophils are isolated from the peripheral blood of normal human volunteers by the method of Hansel et al. (Hansel, T. T., et al., *J. Immunol. Methods*, 145, 105 (1991)) with minor modifications (Ide, M., et al., *J. Immunol. Methods*, 168, 187 (1994)). A column for performance of magnetic activated cell sorting (MACS), which can separate up to $2 \times 10^9$ cells with yield efficiencies that are comparable to those obtained with the smaller MACS columns, is employed. Individuals are selected who have eosinophils around the upper limit of normal, approximately $0.5 \times 10^9$/L, so that between $30-40 \times 10^6$ eosinophils can be obtained. These numbers are sufficient for virtually all of the experiments described below.

B. Effects on IL-5 Stimulated Eosinophil Functions

The ability of 1 µM dexamethasone, 1 mM lidocaine, 100 µM glyburide, and 10 µM cromakalim to alter IL-5 stimulated eosinophil functions is tested in various assays. These IL-5 mediated eosinophil function assays include: 1) superoxide production (Horie, S., Kita, H. *J. Immunol.*, 152, 5457 (1994)), 2) degranulation (Kita, H., et al., *J. Immunol.*, 149, 628 (1992)), and 3) enhancement of IgG and sIgA mediated eosinophil differentiation from umbilical cord mononuclear cells (Ten, R. M., et al., *Cytokine*, 3, 350 (1991)). In these experiments, concentration-response curves are performed using concentrations found active in preliminary experiments employing the eosinophil survival assay, e.g., lidocaine up to 1 mM, glyburide up to 100 μM, dexamethasone up to 1 μM, and, finally, cromakalim up to 10 μM.

C. Mechanisms of Action of Glucocorticoid and Glucocorticomimetic Agents

1. Effects of IL-5 Signal Transduction

Prior studies of IL-5 mediated signal transduction have shown that IL-5 induces tyrosine phosphorylation of Lyn kinase and activation of Lyn kinase and Raf kinase (Pazdrak, K., et al., *J. Exp. Med.*, 181, 1827 (1995)). In addition, IL-5 stimulated phosphorylation of MEK, and tyrosine phosphorylation and activation of MAP kinases, as well (Pazdrak, K., et al., *J. Exp. Med.*, 181, 1827 (1995)). IL-5 also activates Jak-2, a member of the JANUS family of tyrosine kinases, and induces DNA binding activity of Stat-1α (Pazdrak, K., et al., *J. Exp. Med.*, 181, 1827 (1995); Pazdrak, K., et al., *J. Immunol.*, 155, 397 (1995)).

For experiments with MAP kinase, eosinophils are incubated with ~$10^{-10}$ M IL-5 for varying periods of time at 37° C. in the presence and absence of dexamethasone from $10^{-9}$ M to $10^{-6}$ M, with lidocaine from $10^{-5}$ M to $10^{-3}$ M, and with glyburide from $10^{-6}$ M to $10^{-4}$ M. Cells are pelleted by centrifugation, washed and lysed in 10% Triton X-100 containing phenylmethylsulfonyl fluoride (PMSF), 2 μg/ml aprotinin, 2 mM EDTA, 1 μg/ml pepstatin and 1 mM $Na_3VO_3$ (Pazdrak, K., et al., *J. Exp. Med.*, 181, 1827 (1995)). Lysates are precleared by incubation with protein A agarose, and then incubated with a monoclonal antibody specific for MAP kinase 1–5 μg/ml, (Santa Cruz Biotechnology Inc., Santa Cruz, Calif.). Immune complexes bound to protein A agarose are washed, suspended in kinase buffer (10 mM HEPES, pH 7.4,50 mM NaCl, 5 mM $MgCl_2$, 5 mM $MnCl_2$ and 0.1 mM $Na_3VO_4$) and their ability to phosphorylate myelin basic protein 0.5 ng/ml in the presence of [γ-$^{32}$P] ATP tested. After incubation for 15 minutes, the reaction mixture is spotted on phosphocellulose paper and after thorough washing, radioactivity measured. Prior experiments have shown an approximately threefold increase in MAP kinase activity after incubation of eosinophils with $10^{10}$ M IL-5 (~4 ng/ml) (Pazdrak, K., et al., *J. Exp. Med.*, 181, 1827 (1995)).

The ability of IL-5 to activate Jak-2 tyrosine kinase and Stat-1 is also tested as described previously (van der Bruggen, T., et al., *Blood*, 85, 1442 (1995); Pazdrak, K., et al., *J. Immunol.*, 155, 397 (1995)). IL-5 at $1 \times 10^{-10}$ M is used to stimulate eosinophils over varying periods of time at 37° C., and the reaction terminated by addition of one volume of ice-cold PBS containing 1 mM $Na_3VO_3$. Cells are washed, lysed, centrifuged, precleared with protein A agarose and incubated with rabbit polyclonal anti-Jak-2 (Santa Cruz Biotechnology) for 4–6 hours at 4° C. Immunoprecipitates are washed, suspended in kinase buffer (10 mM HEPES, pH 7.4, 50 mM NaCl, 5 mM $MgCl_2$, 5 mM $MnCl_2$ and 0.1 mM $Na_3VO_4$) with [γ$^{32}$P] ATP for 60 minutes at room temperature. After washing three times with lysis buffer, the kinase reaction products are analyzed by SDS-PAGE and autoradiography.

Stat-1α is analyzed by immunoprecipitation using a polyclonal antibody against p91 (Transduction Laboratories, Lexington, Ky.) followed by SDS-PAGE, blotted on Hybond membranes, reacted with antiphosphotyrosine (clone 4G10) (Upstate Biotechnology, Lake Placid, N.Y.), and the reaction developed using enhanced chemiluminescence per the manufacturer's recommendations. Stat-1 proteins in the eosinophil nuclear extract are analyzed by the electrophoretic mobility shift assay using the GAS probe labeled with [γ$^{32}$P] ATP (van der Bruggen, T., et al., *Blood*, 85, 1442 (1995); Pazdrak, K., et al., *J. Immunol.*, 155, 397 (1995)).

2. Effects on the Transcription Factors NFκB and IκBα

One mechanism by which glucocorticoids exert their immunosuppressive effect is through the inhibition of the transcription factor NFκB (Scheinman, R. I., et al., *Science*, 270, 283 (1995) Auphan, N., et al., *Science*, 270, 286 (1995)). This inhibition is mediated through an increase in the rate of synthesis of IκBα, a cytosolic inhibitor of NFκB, and has been documented in several T cell lines and a monocytic cell line. Because lidocaine and glyburide mimic glucocorticoid activity in eosinophils, it is possible that these agents also act through the upregulation of IκBα. Eosinophils are pretreated with dexamethasone, lidocaine, and glyburide, using the concentration ranges described above, followed by stimulation with IL-5 at $10^{-10}$ M. The IκBα protein levels are analyzed utilizing a commercially available anti-IκBα antibody (Santa Cruz Biotechnology, Santa Cruz, Calif.) and Western blotting. Normal donors with high levels of circulating eosinophils are employed for these experiments. Initially, 1 μM dexamethasone, $10^{-3}$ M lidocaine and $10^{-4}$ M glyburide are incubated with cells for up to 4 hours and then the level of IκBα determined. The induction of NFκB DNA binding activity in eosinophils by IL-5 is also determined, using procedures described by Scheinman et al. (Scheinman, R. I., et al., *Science*, 270, 283 (1995)).

3. Determination Whether the High Affinity Sulfonylurea Receptor (SUR) Is Present on Eosinophils The abilities of glyburide and lidocaine to block IL-5 mediated eosinophil survival suggests that eosinophils possess a SUR and possibly an ATP-sensitive potassium channel, $I_{KATP}$. Because glyburide inhibits IL-5 mediated eosinophil function, the human eosinophil may express SUR. To test this hypothesis, direct binding of a fluorescinated derivative of glyburide to peripheral blood cells is tested by FACS. The fluorescent glyburide compound, N(4, 4-difluoro-5, 7-dimethyl-3α, 4α-diaza-S-indicene-3-propionyl) cysteic-glyburide (BODIPY-glyburide, Molecular Probes, Eugene, Oreg.) is incubated at concentrations ranging from $10^{-4}$ M to $10^{-9}$ M with test cells in the presence and absence of 100× molar excess of glyburide, washed thoroughly and analyzed by FACS. Because washing of cells before FACS may result in dissociation of BODIPY-glyburide, a fluorescent microscope is employed to observe any membrane fluorescence ringing the eosinophil. As a positive control, HIT-T15 cells (ATCC, Rockville, Md.), which possess the high affinity 140 kDa SUR (Santerre, R. F., et al., *Proc. Natl. Acad. Sci. USA*, 78, 4339 (1981)), are propagated and tested with varying concentrations of BODIPY-glyburide to establish optimal conditions for binding and detection by FACS.

Preliminary studies testing this concept have failed to show significant binding, suggesting eosiniphil SUR differs from the classical SUR of the pancreatic β-islet cells.

To determine whether mRNA is present in whole buffy coat cells from normal persons and from purified eosinophils using HIT-T15 cells as a positive control, RT-PCR analyses using primers specific for human SUR (Aguilar-Bryan, L., et al., *Science*, 268, 423 (1995); Thomas, P. M., et al., *Science*, 268, 426 (1995)) and Kir6.2 (Sakura, H.,et al., *FEBS Lett.*, 377, 338 (1995)), are employed.

Patch clamp experiments are also performed to test whether $I_{KATP}$ is present on purified eosinophils, whether IL-5 alters the functioning of the channels, and whether lidocaine and glyburide affect their function.

4. Analyses of the Effects of Glucocorticoids and Glucocorticomimetic Agents on a Murine Model of the Allergen-induced Eosinophil-rich Late Phase Reaction A murine model of the allergen-induced IgE-mediated eosinophil-rich late phase reaction induced by immunization of BALB/c mice with ragweed extract is available (Kaneko et al., *Int. Arch. Allergy Appl. Immunol.*, 96, 41 (1991)). In this model, mice are sensitized by a series of five injections of a ragweed pollen extract and on day 20 are challenged by an intraperitoneal injection of 0.2 ml of a 1:1,000 dilution of ragweed pollen extract (Greer Laboratories, Inc., Lenoir, N.C.). Forty-eight hours after challenge, peritoneal lavage fluids are collected, and the numbers and kinds of cells determined by total and differential leukocyte counts (after staining of the peritoneal cells with May-Grunwald-Giemsa stain). With this model, marked eosinophilia occurs at 48 hours and is associated with eosinophil degranulation. RT-PCR analyses have shown that peritoneal cells express IL-5. In addition, eosinophil degranulation is estimated by measuring EPO activity in peritoneal fluids using o-phenylendiamine as substrate.

To test the effectiveness of glucocorticoids, lidocaine, and glyburide on the allergen-specific late phase reaction, lidocaine is administered by intraperitoneal injection 6 hours prior to allergen challenge, and blood lidocaine levels of ~2–5 µg/ml are maintained using an ALZA pump implanted in the peritoneal cavity. Lidocaine levels are measured in the peritoneal cavity and in the blood of the BALB/c mice by an immunoassay, which can detect lidocaine levels as low as 0.1 µg/ml (available in the Department of Laboratory Medicine, Mayo Clinic, Rochester, Minn.). Similarly, glyburide is tested for its ability to alter the degree of eosinophilia and eosinophil degranulation occurring in this model. The hypoglycemia expected from glyburide treatment is circumvented by treating mice with 100 mg streptozocin to ablate pancreatic βcells. The streptozocin-treated animals are immunized as described above, and the peritoneal late phase reaction induced in the presence and absence of glucocorticoids and the glucocorticomimetic drugs.

Pulmonary late phase reactions may also be used, because of the ability to administer high concentrations of lidocaine and glyburide to the lung by local instillation in such reactions. For example, the doses of lidocaine administered to patients are in the hundreds of milligrams, and yet blood levels in the patients do not rise above 2 µg/ml. For the experiments described above, it may be desirable to give large doses of agents of the invention. If the desired concentrations of drugs with the peritoneal model of the late phase reaction cannot be achieved, the same reagents can be employed to sensitize mice by pulmonary challenge and elicitation of BAL eosinophilia and eosinophil degranulation. Alternatively, other SUR active agents, such as tolbutamide, glipizide, or gliclazide, can be utilized for these experiments.

5. Effects of Glucocorticomimetic Agents on Cytokine Stimulation of Cells Other Than Eosinophils The effects of lidocaine and glyburide are compared to glucocorticoids by measuring cytokine-enhanced histamine release from anti-IgE stimulated basophils (Hurai et al., *J. Exp. Med.*, 172, 1525 (1990); Hirai, K., et al., *J. Immunol.*, 141, 3958 (1988)). Briefly, peripheral blood basophils are isolated from venous blood of normal individuals by Ficoll-Hypaque density gradient centrifugation, as described by (O'Donnell, M. C., et al., *J. Exp. Med.*, 157 1981 (1983)). These cell preparations contain 1–3% basophils as determined by alcian blue, and histamine release is induced by exposure to anti-IgE. Histamine is measured by ELISA using a commercially available kit (Immunotech, Westbrooke, Me.), and the effect of IL-3, IL-5 and GM-CSF on histamine release determined using concentrations of these cytokines ranging from picogram/ml to as high as 50 ng/ml. The ability of the glucocorticomimetics to inhibit IgE-mediated histamine release is analyzed using concentrations between $10^{-7}$ M and $10^{-3}$ M. The effect of cromakalim is also tested to determine whether it synergizes with cytokines in the basophil histamine release.

The effects of glucocorticoids and the glucocorticomimetic agents on T cell clones is then analyzed. Initially, the abilities of these agents to inhibit production of IL-2 and IL-4 is analyzed using T cell clones producing IL-2 or IL-4 on stimulation with anti-CD3. IL-2 or IL-4 in supernatants is measured by ELISA using kits (R&D, Minneapolis, Minn.). Then, the ability of the clones to proliferate in response to exogenous IL-2 or IL-4 is tested using $^3$H-thymidine uptake as a measure of cell proliferation.

EXAMPLE III

Effects of Sulfonylureas on Isolated Human Eosinophils

The effects of sulfonylureas on isolated human eosinophils were determined by utilizing in vitro assays of eosinophil survival and eosinophil activation (superoxide production).

A. Eosinophil Isolation

Human eosinophils were isolated by layering over Percoll and separated from remaining neutrophils by negative selection using anti-CD16 magnetic beads and MACS column isolation. The isolated eosinophils were >97% pure. All drugs were purchased from Sigma unless otherwise noted. Human recombinant IL-5 was generously provided by Schering Corporation. Sulfonylureas were resuspended in DMSO, and dilutions of sulfonylurea stock solutions were made in Hybricare medium containing 10% alpha calf serum. The concentration of DMSO in the glyburide solution added to the eosinophils never exceeded 2% (final concentration <0.5%).

B. Eosinophil Survival Assay

Isolated eosinophils were incubated in 96-well plates at $0.25\times10^6$ Eos/mL with various concentrations of IL-5 plus or minus experimental drugs in a total volume of 200 µL. The eosinophils were incubated for 4 days at 37° C. and 5% $CO_2$. To determine percent survival, the total volume of each well was transferred to a separate 12×75 polystyrene tube and stained with 200 µL of a 0.5 mg/mL propidium iodide solution. The sample was then analyzed on a Becton Dickenson FACScan flow cytometer for PI fluorescence. The percentage of surviving eosinophils is defined as the number of PI-negative eosinophils over the total number of eosinophils gated and analyzed.

C. Superoxide Assay

Isolated eosinophils were incubated in a 96-well plate at $0.25\times10^6$ Eos/mL with 1.2 mg/mL Cytochrome C and various concentrations of IL-5 plus or minus a 30 minute pretreatment with experimental drugs. Total volume per well was 200 µL. The entire plate was read at $OD_{550}$ on a Molecular Devices ThermoMax plate reader, and readings recorded every 15 minutes for 2 to 3 hours.

Figure 3A:
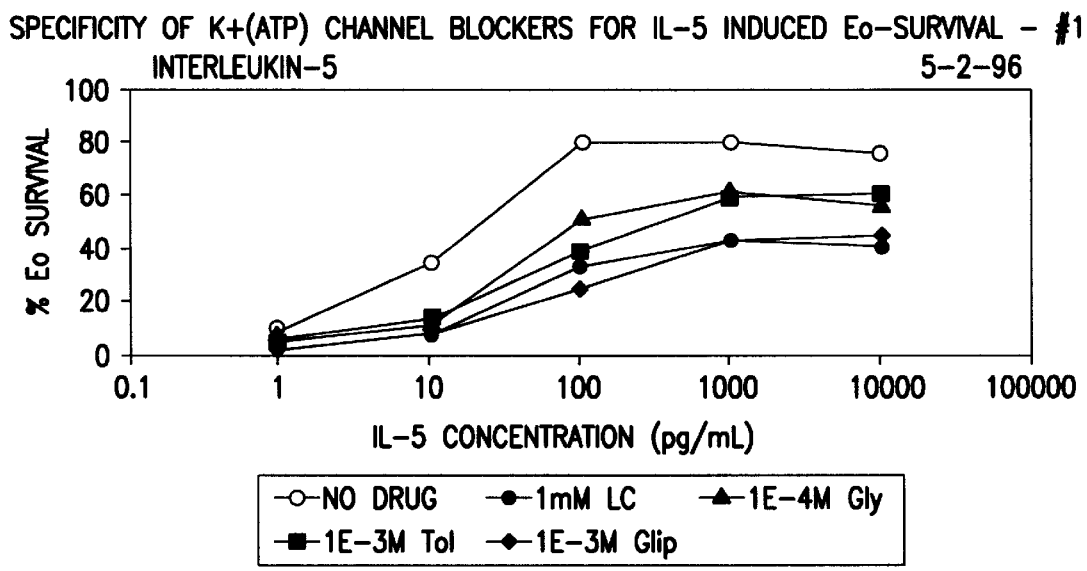
FIG. 3: Graphs of the results of incubation of isolated human eosinophils with the sulfonylureas glyburide (gly), tolbutamide (tol) or glipizide (glip), as described in Example III (C).
Figure 3B:
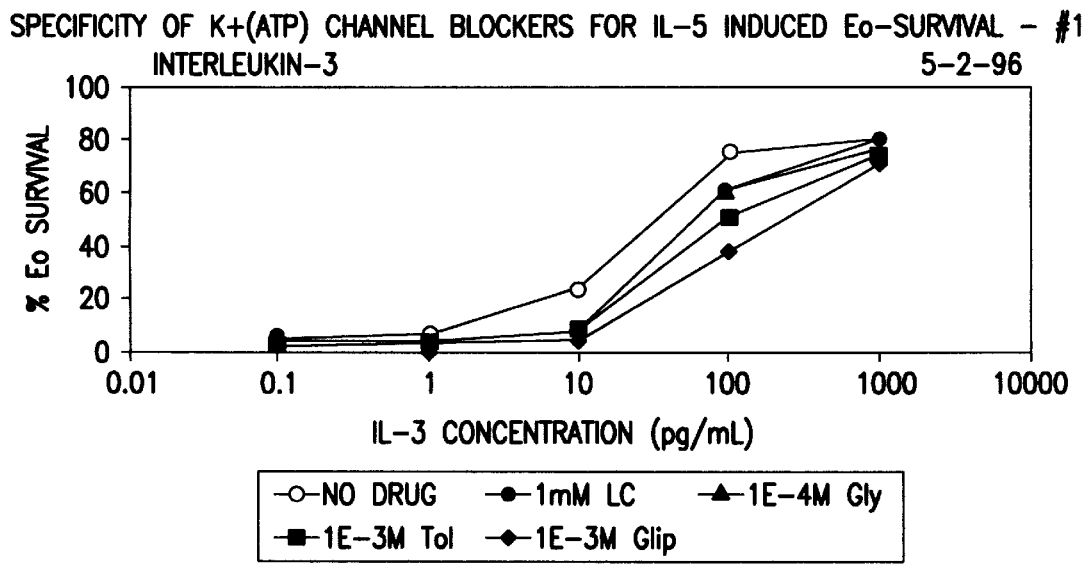
Figure 3C:
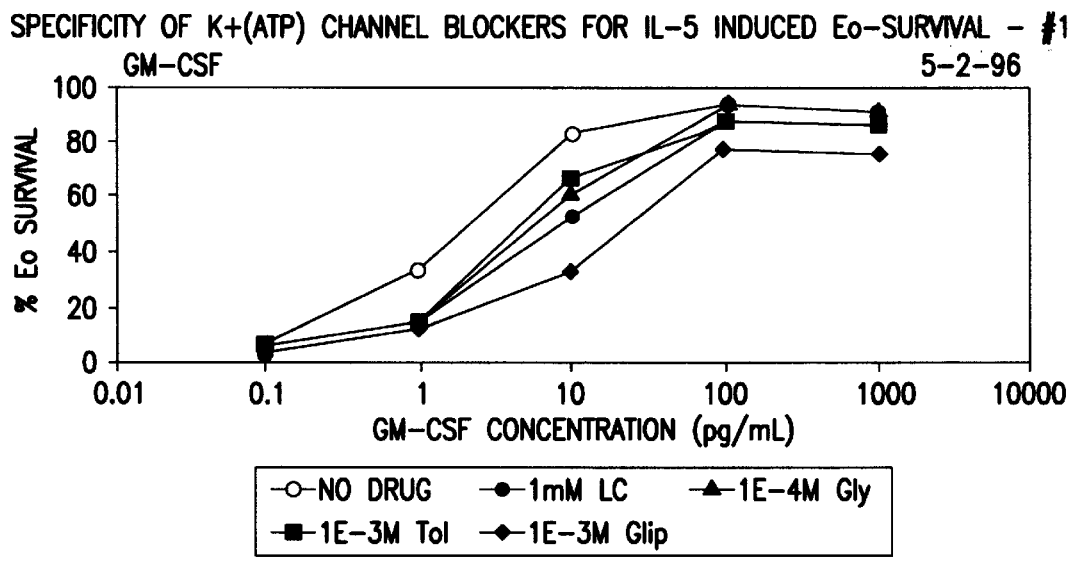

Treatment of eosinophils with IL-5, IL-3 or GM-CSF results in a concentration-dependent survival of the cells. Incubation of isolated human eosinophils with the sulfonylureas glyburide (gly), tolbutamide (tol), or glipizide (glip) results in the concentration-dependent inhibition of cytokine-mediated survival. (See FIG. 3). Although high concentrations of IL-3 and GM-CSF can overcome the sulfonylurea-mediated inhibition, even concentrations as high as 10,000 pg/mL IL-5 cannot reverse the effects of the drugs. Thus, the sulfonylureas glyburide, tolbutamide, and glipizide inhibit cytokine-driven eosinophil survival in vitro, and IL-5-mediated survival is particularly susceptible.

Figure 4:
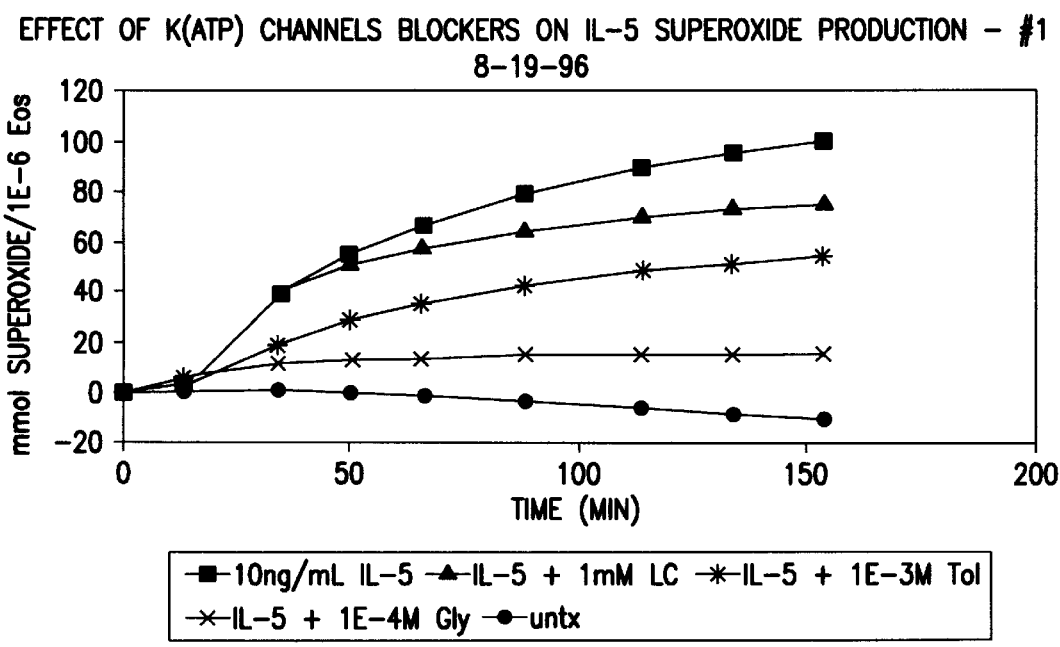
FIG. 4: Graph of the results of cytokine-induced superoxide production by eosinophils is inhibited by the sulfonylureas glyburide and tolbutamide, as described in Example III (C).

Cytokine-induced superoxide production by eosinophils is inhibited by the sulfonylureas glyburide and tolbutamide. (See FIG. 4). Stimulation of purified human eosinophils with 10 ng/mL IL-5 results in a time-dependent increase in superoxide production. Co-treatment of IL-5-stimulated eosinophils with lidocaine or the sulfonylurea tolbutamide inhibits the superoxide production moderately, whereas co-treatment with glyburide almost completely blocks cytokine-induced superoxide production. Co-treatment of IL-5-stimulated eosinophils with 1 $\mu$M dexamethasone has no effect in this assay (data not shown). Thus, the sulfonylureas are a unique class of inhibitors of eosinophil activation, and glyburide in particular is more potent than either dexamethasone or lidocaine.

EXAMPLE IV

Synergistic Effects of Simultaneous Administration of Two Compounds

A. Eosinophil Purification

Eosinophils were purified from peripheral blood, as previously described (Hansel et al., *J. Immunol. Method*, 145, 105 (1991); Ide et al., *J. Immunol. Methods*, 168, 187 (1994)). Briefly, 60 ml of heparinized venous blood was obtained from normal volunteers or volunteers with mild to moderate asthma or allergic rhinitis. Eosinophils were purified by separation from low density blood components by centrifugation through 1.082 Percoll (Sigma), by erythrocytelysis with sterile $H_2O$, and by magnetic activated cell sorting (MACS) with immunomagnetic CD16 beads (Miltenyi Biotec Inc., Auburn, Calif.). This procedure yielded eosinophils of >95% purity by phloxine and methylene blue staining; the remaining cells were neutrophils. Cells were initially suspended on ice in a 1×piperazine-N, N'-bis(2-ethane sulfonic acid) (PIPES) (25 mM PIPES, 50 mM NaCl, 5 mM KCl, 25 mM NaOH, 5.4 mM glucose) buffer, centrifuged at 400 g, 4° C., for 10 minutes and resuspended in Hybri-Care medium (American Type Culture Collection, Rockville, Md.) containing gentamicin 50 $\mu$g/ml (Sigma), 10% defined calf serum and 200 mM L-glutamine 1%, and immediately placed in culture.

B. Eosinophil Survival Assay

The eosinophil survival assay was performed, as described previously (Wallen et al. *J. Immunol.*, 147, 3490 (1991)), but enhanced for increased precision. Briefly, purified eosinophils, 100 $\mu$l suspension, were placed in a 96-well, full area, flat bottom tissue culture place (Falcon #3072, Becton Dickinson, Lincoln Park, N.J.) at 2×10$^4$ cells/well. Pharmacologic agents were added in 50 $\mu$l aliquots to yield final concentrations of 0.01 nM to 1000 nM. Cytokines, 50 $\mu$l, were added to yield final concentrations of 1 to 1000 pg/ml (IL-5), 0.1 to 100 pg/ml (GM-CSF) and 1 to 1000 pg/ml (IFN-$\gamma$). Hybri-Care medium was added to each well for a final volume of 200 $\mu$l/well. After incubation at 37° C. and 5% $CO_2$ for up to four days, the entire cell suspension was transferred to 12×75 polystyrene round-bottom tubes and placed on ice if a delay of one hour or longer was expected. An equal volume (200 $\mu$l) of PI solution was added to the cell suspension to provide a final concentration of 0.50 $\mu$g/ml PI. Cell counting was performed by flow cytometry (FACScan Becton Dickinson). Viable cells were calculated as the percentage of intact cells not stained with PI divided by the total number of intact cells.

C. Glyburide and Dexamethasone Synergy

Figure 5:
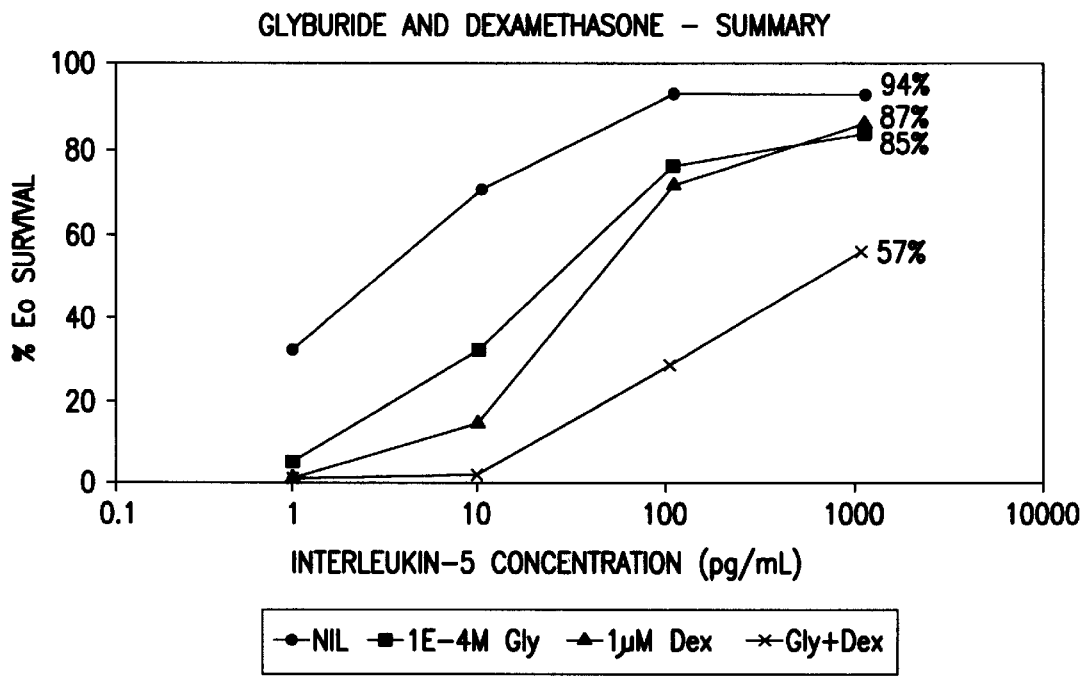
FIG. 5: Graph of the results of co-administration of glyburide and dexamethasone synergy as shown by eosinophil survival assay, as described in Example IV (C).

The results of the eosinophil survival study using glyburide and dexamethasone are depicted in FIG. 5.

The eosinophil survival is plotted on the y axis as a percentage of the total number of eosinophils and increasing concentrations of IL-5 in pg/ml is plotted on the x axis. Increasing concentrations of IL-5 from 1–1000 pg/ml induce increasing levels of eosinophil survival up to a maximum of approximately 94% at 1000 pg/ml IL-5. Coincubation of IL-5 stimulated eosinophils with 1 $\mu$M dexamethasone results in the shift of the curve to the right indicating that dexamethasone is inhibiting the IL-5 induced survival of the eosinophils. At 1000 pg/ml IL-5, there is 87% eosinophil survival in the presence of dexamethasone, whereas there is 94% survival in the absence of dexamethasone.

The same is true for coincubation of IL-5 treated eosinophils with $1 \times 10^{-4}$ M glyburide shown in the squares. The survival curve indicates that glyburide also inhibits eosinophil survival as driven by IL-5. At 1000 pg/ml IL-5 and $1 \times 10^{-4}$ M glyburide, maximal survival of the eosinophils is 85% as compared to 94% in the absence of glyburide. If glyburide and dexamethasone exhibit an additive effect when incubated together with IL-5, one would expect to see a 78% survival rate when eosinophils were incubated with 1000 pg/ml IL-5, 1 $\mu$M dexamethasone and $1 \times 10^{-4}$ M glyburide. Experimentally, the maximal survival at 1000 pg/ml IL-5 in the presence of both dexamethasone and glyburide is only 57%. Thus, glyburide and dexamethasone also synergize to inhibit eosinophil survival.

D. Lidocaine and Glyburide Synergy

Figure 6:
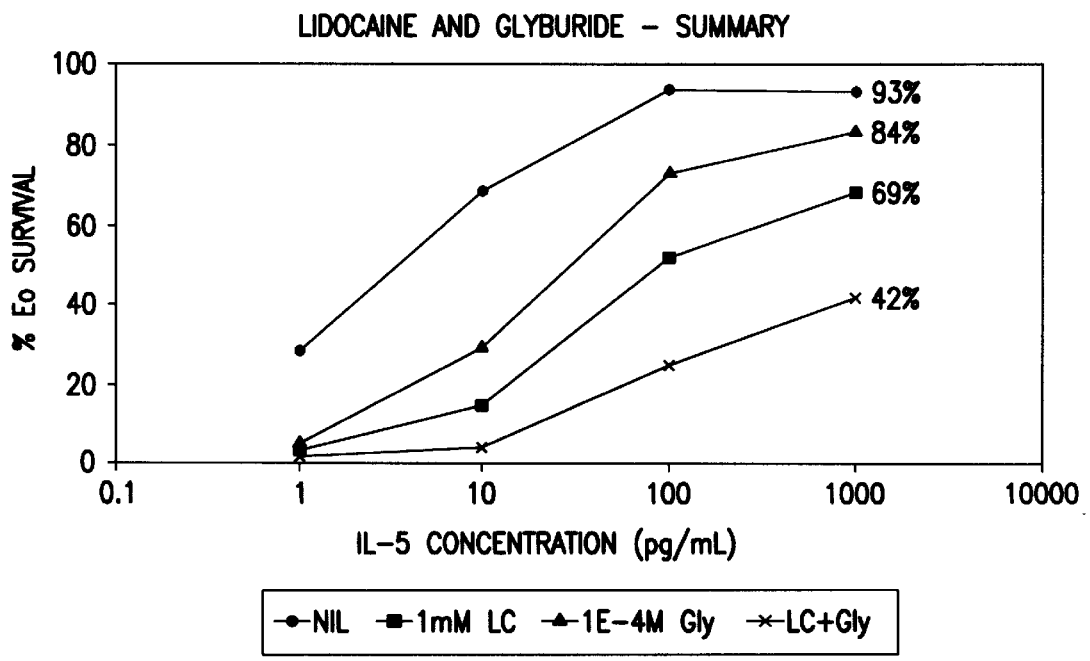
FIG. 6: Graph of the results of co-administration of glyburide and lidocaine synergy as shown by eosinophil survival assay, as described in Example IV (D).

The results of the eosinophil survival study using glyburide and lidocaine are depicted in FIG. 6.

Once again the percentage of eosinophil survival is plotted on the y axis and IL-5 concentration in pg/ml increases on the x axis. Addition of increasing concentrations of IL-5 to the eosinophils results in increasing survival, up to a maximal survival rate of 93% at 1000 pg/ml IL-5. Coincubation of these eosinophils with $1 \times 10^{-4}$ M glyburide and IL-5 results in inhibition of eosinophil survival mediated by IL-5 as indicated by the shift of the triangle curve to the right. Coincubation of these eosinophils with 1000 pg/ml IL-5 and glyburide results in the maximal survival of 84%, whereas the survival is 93% in the absence of glyburide.

A similar, but more striking, result is seen with coincubation of the eosinophils with IL-5 and 1 mM of lidocaine shown in the squares. At 1000 pg/ml IL-5 and 1 mM lidocaine, maximal survival of eosinophils is 69% as compared with 93% in the absence of lidocaine. If the inhibitory effects of lidocaine and glyburide are additive, one would expect to see a final survival rate of approximately 62%. However, coincubation of eosinophils with IL-5, lidocaine and glyburide resulted in a maximal survival of 42% at 1000 pg/ml of IL-5. Thus, glyburide and lidocaine also synergistically interact to inhibit IL-5 driven eosinophil survival.

EXAMPLE V

A. Effect of K$^+$ Channel Blockers on Eosinophil Survival

To test the hypothesis that K$^+$ channels are involved in eosinophil survival, the activities of three different K$^+$ channel blockers (glyburide, tetraethylammonium (TEA) chloride, and apamin) were compared with the activity of lidocaine on IL-5 stimulated eosinophils. Glyburide is a blocker of ATP-sensitive K$^+$ channels, TEA blocks K$^+$ channels and is a nicotinic cholinergic receptor antagonist, and apamin blocks Ca$^{2+}$ activated K$^+$ channels (Sturgess, N. C., et. al., *Lancet* 8453:474(1985))(Gallin, E. K., et. al., *Inflammation: Basic Principles and Clinical Correlates, Second Edition*, J. I. Gallin, I. M. Goldstein, and R. Snyderman (eds) Raven Press Ltd, NY(1992)).

Figure 7A:
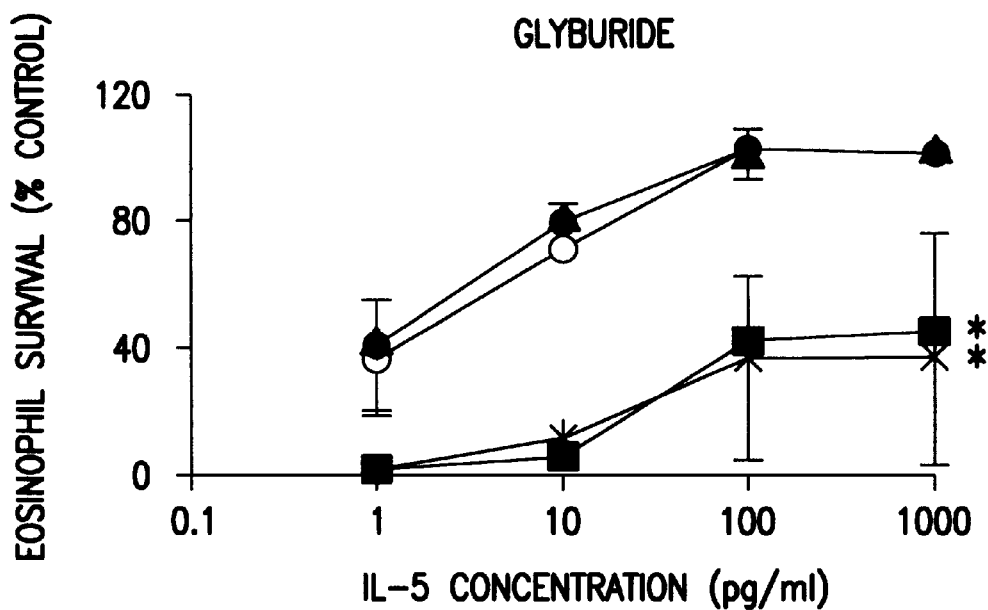
FIG. 7: Graph of the results of an eosinophil survival assay, showing glyburide, an ATP-sensitive K+ channel blocker, inhibiting eosinophil survival, as shown in Example V (A).
Figure 7B:
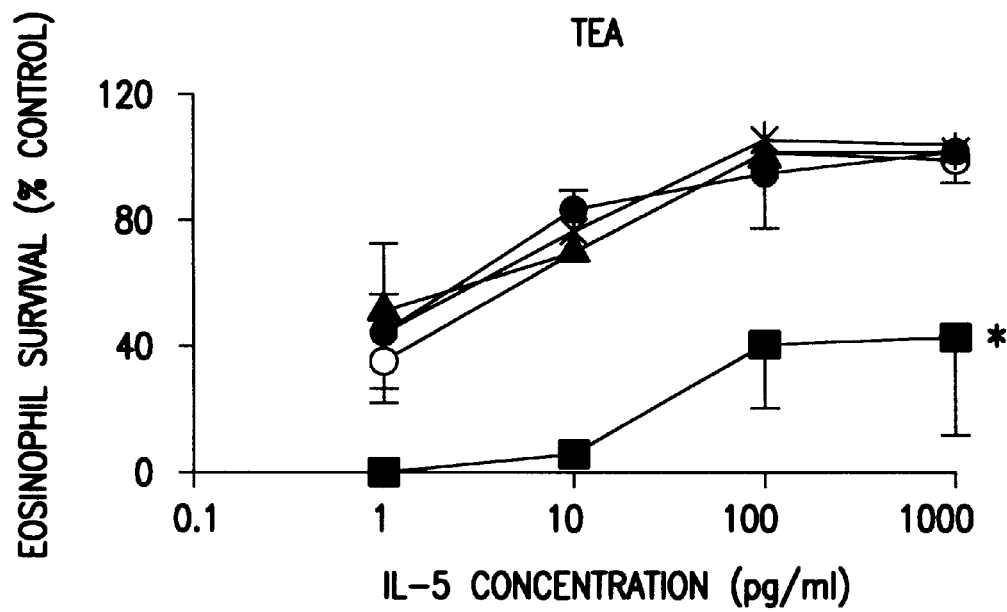
Figure 7C:
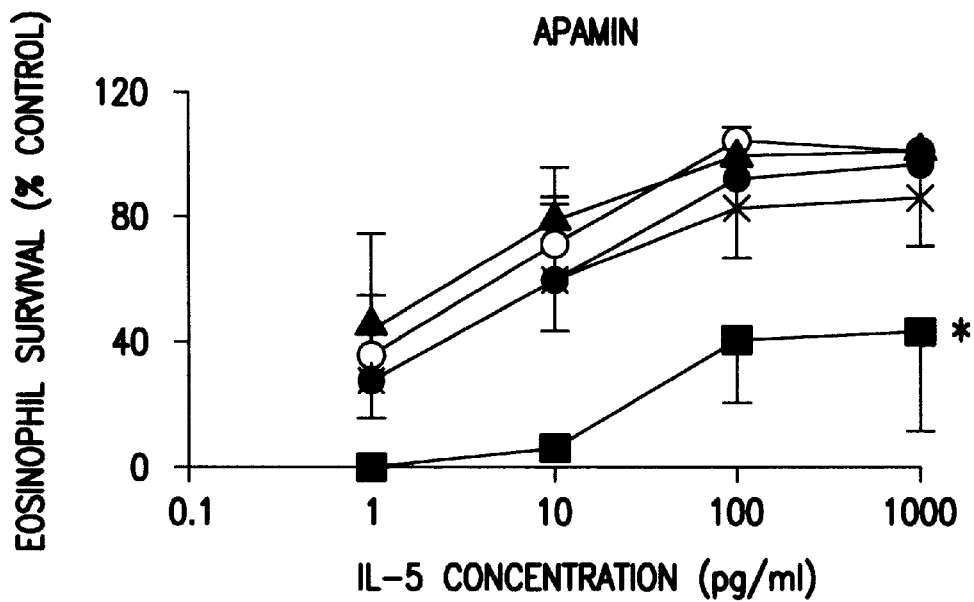

To test whether glyburide, an ATP-sensitive K$^+$ channel blocker, inhibits eosinophil survival, purified eosinophils were cultured for four days with increasing concentrations of IL-5 in the presence of different inhibitors. The results of this experiment are depicted in FIG. 7. Survival was assayed and is plotted as a percentage of eosinophil survival at 1000 pg/ml IL-5. Each panel shows the means (± standard deviations) of at least three independent experiments using cells from both normal and allergic patients. Eosinophils were treated with IL-5 in the presence of medium control (○), $1 \times 10^{-3}$ M lidocaine (■), or various concentrations of drugs. Top panel: glyburide (▲=$10^{-6}$ M, ●=$10^{-5}$ M, *=$10^{-4}$ M); Center panel: tetraethylammonium (TEA) chloride (▲=$10^{-5}$ M, ●=$10^{-4}$ M, * =$10^{-3}$ M); Bottom panel: apamin (▲=$10^{-7}$M, ●=$10^{-6}$ M, *=$10^{-5}$ M). The asterisk (*) indicates p<0.05 (compared to 1000 pg/ml IL-5 alone).

As shown in FIG. 7, TEA and apamin had no significant effect on IL-5 induced eosinophil survival. Only glyburide ($1 \times 10^{-4}$ M) inhibited IL-5 mediated eosinophil survival as effectively as lidocaine.

Figure 8:
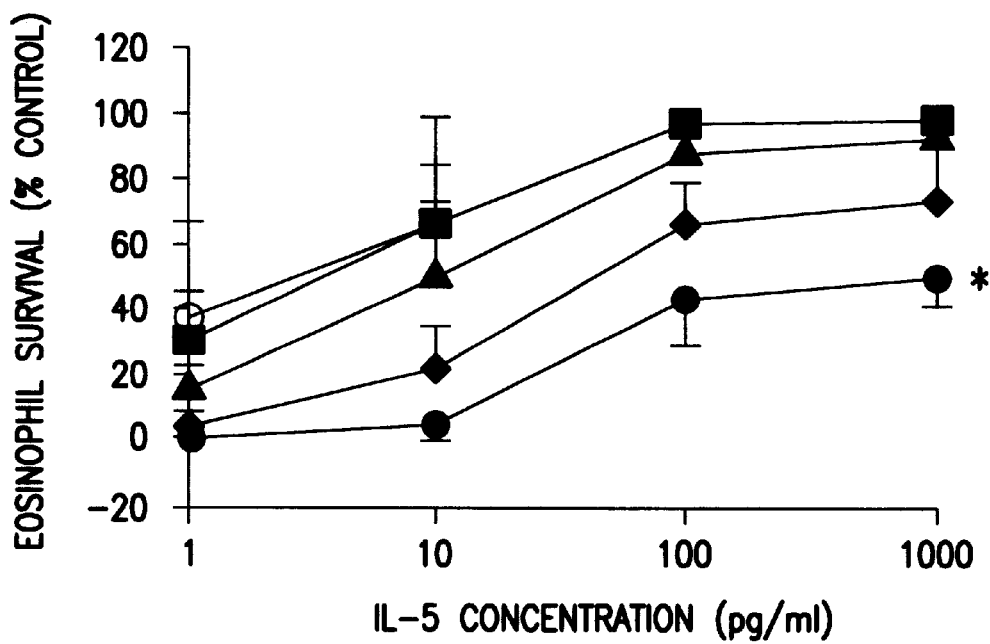
FIG. 8: Graph of the results of glyburide's dose-dependent inhibition of eosinophil survival, as described in Example V (A).
Figure 9A:
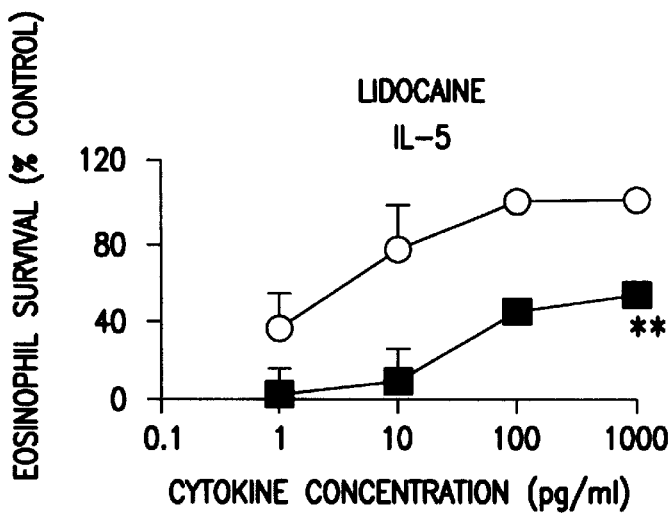
FIG. 9: Graph depicting the preferential inhibition of IL-5 mediated eosinophil survival by glyburide, as described in Example V (A).
Figure 9B:
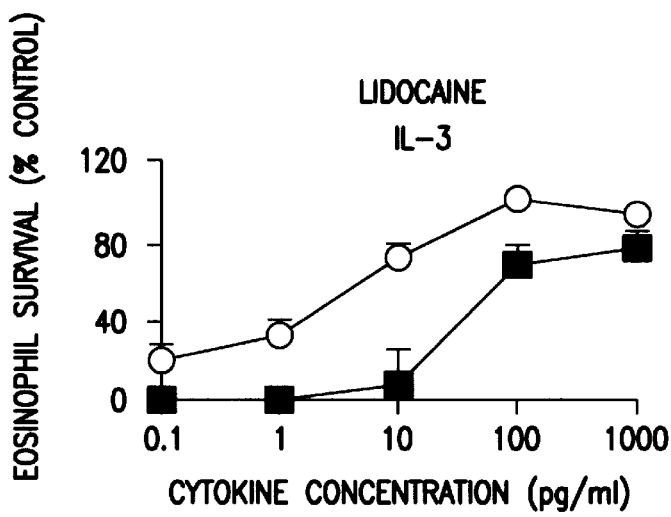
Figure 9C:
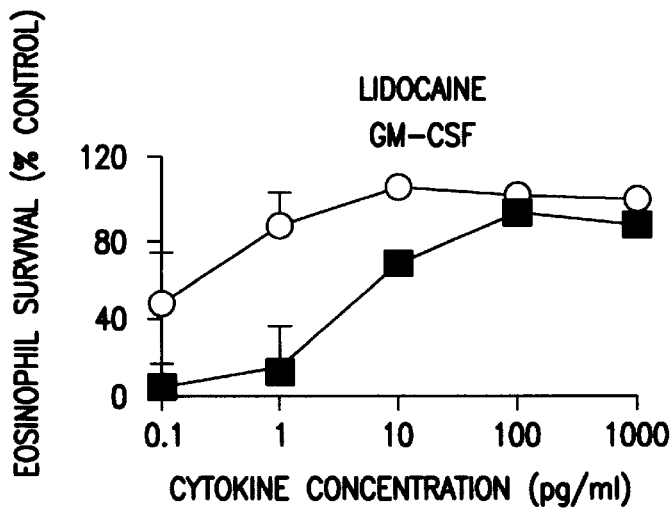
Figure 9D:
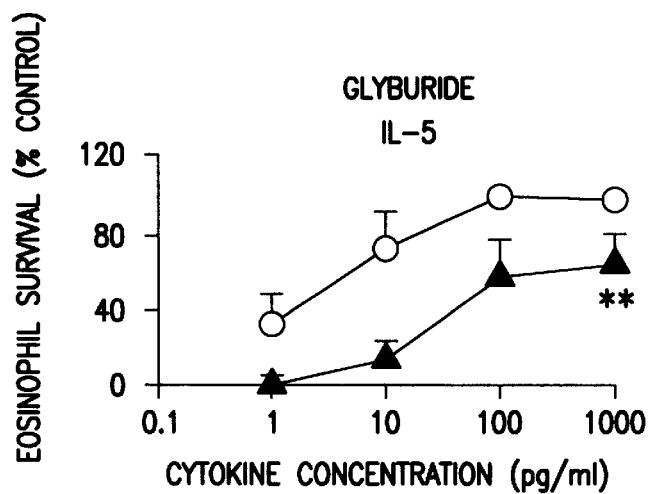
Figure 9E:
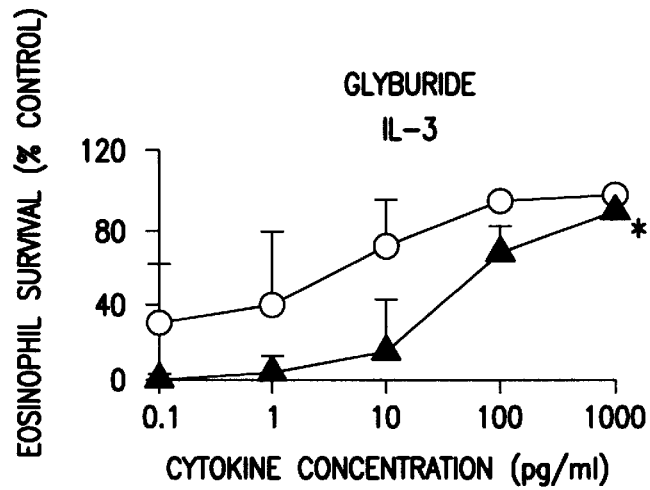
Figure 9F:
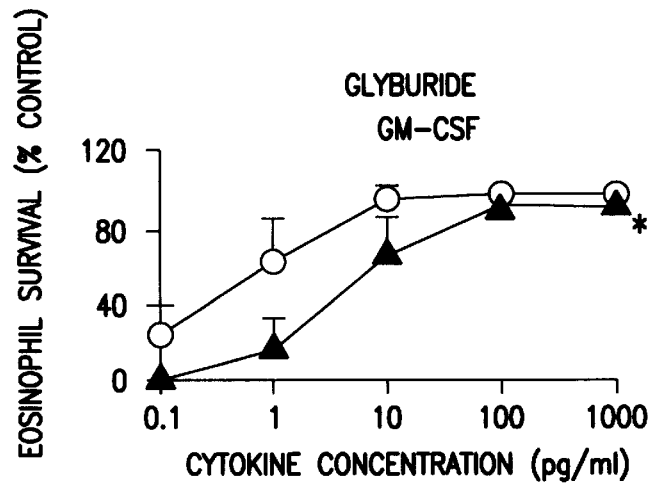

To determine whether this was a dose-response effect, doses of glyburide between $10^{-5}$ M and $10^{-4}$ M were tested. Purified eosinophils were cultured for four days with various concentrations of IL-5. Survival was assayed and the results are depicted in FIG. 8. Survival is plotted as a percentage of eosinophil survival at 1000 pg/ml IL-5. Shown are the means (± standard deviations) of three independent experiments using eosinophils from both normal and allergic donors. Eosinophils were co-cultured with IL-5 and medium control (○) or glyburide (■=$1 \times 10^{-5}$ M, ▲=$3.3 \times 10^{-5}$ M, ♦=$6.7 \times 10^{-5}$ M, ●=$1 \times 10^{-4}$ M). The asterisk (*) indicates p<0.05 (compared to 1000 pg/ml IL-5 alone).

As shown in FIG. 8, glyburide does exhibit a dose-response effect, which is especially evident at lower IL-5 concentrations. However, only the inhibition mediated by $10^{-4}$ M glyburide was statistically significant.

One of the characteristics of lidocaine inhibition of eosinophil survival is a relative specificity for IL-5. To see if glyburide exhibits a similar preference, the ability of glyburide to inhibit eosinophil survival mediated by IL-3 and GM-CSF was examined. Purified eosinophils were cultured for four days with various concentrations of IL-5, IL-3, or GM-CSF. Eosinophil survival was analyzed and is depicted in FIG. 9. Survival is plotted as a percentage of eosinophil survival at maximal cytokine concentrations. Each panel shows the means (± standard deviations) of at least four independent experiments using eosinophils from both normal and allergic donors. When not visible, the standard deviation was smaller than the symbol. Eosinophils were co-cultured with cytokines and medium control (○), $1 \times 10^{-3}$ M lidocaine (■, left panel) or $1 \times 10^{-4}$ M glyburide (▲, right panel). A single asterisk (*) indicates p<0.05; a double asterisk (**) indicates p<0.005 (compared to 1000 pg/ml cytokine alone).

As shown in FIG. 9, eosinophil survival was inhibited by glyburide at low IL-3 and GM-CSF concentrations, but the inhibition was completely overcome by increased concentrations of these cytokines. This inhibition pattern was identical to that observed with lidocaine. Glyburide and lidocaine both preferentially inhibit IL-5 induced survival as compared to IL-3 or GM-CSF mediated survival, and the inhibition cannot be over come by increased concentrations of IL-5 (up to 10,000 pg/ml; data not shown). Additionally, neither lidocaine nor glyburide mediated a general toxic effect on the cells, as eosinophils stimulated with IL-3 or GM-CSF survived in the presence of the drugs.

Figure 10A:
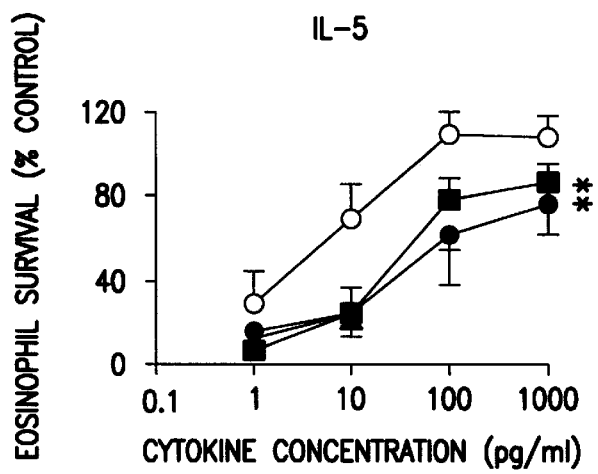
FIG. 10: Graph depicting the preferential inhibition of IL-5 mediated eosinophil survival by sulfonylureas, as described in Example V (A).
Figure 10B:
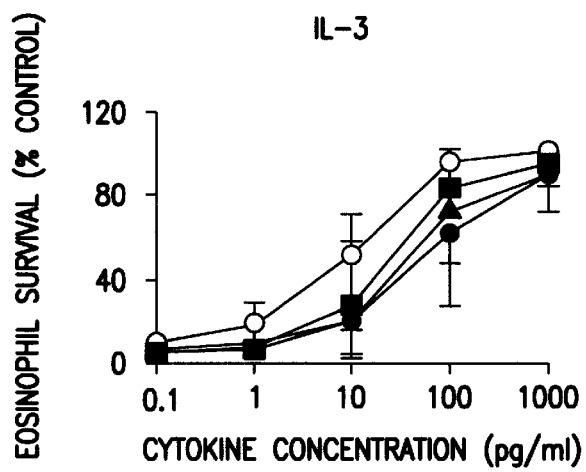
Figure 10C:
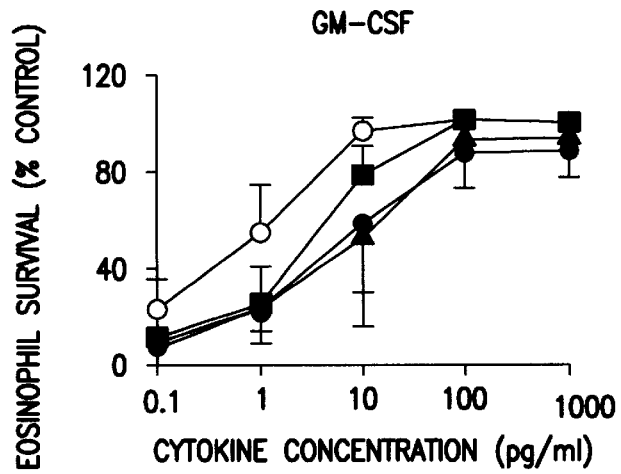

Glyburide, or glybenclamide, belongs to the sulfonylurea family of compounds. Sulfonylureas block ATP-sensitive $K^+$ channels by binding to an accessory regulating receptor, the sulfonyurea receptor (SUR). (Panten, U., et. al., *Exp. Clin. Endocrinol*, 104:1(1996)). To determine whether sulfonylureas other than glyburide also inhibit eosinophil survival by blocking an ATP-sensitive $K^+$ channel, two additional sulfonylureas were examined: tolbutamide and glipizide. Purified eosinophils were cultured for four days with various concentrations of IL-5, IL-3, or GM-CSF in the presence of medium control (○), $1 \times 10^{-4}$ M glyburide (■), $1 \times 10^{-3}$ M tolbutamide (▲), or $1 \times 10^{-3}$ M glipizide (●). Eosinophil survival was analyzed and the results are depicted in FIG. 10. Survival is plotted as a percentage of the eosinophil survival at maximal cytokine concentrations. Each panel shows the means (± standard deviations) of five independent experiments using eosinophils from both normal and allergic donors. The asterisk (*) indicates p<0.05 (compared to 1000 pg/ml cytokine treatment alone).

Results from this test indicated that tolbutamide and glipizide inhibited eosinophil survival as well as did glyburide (see FIG. 10). High concentrations (1000 pg/ml) of IL-3 and GM-CSF overcame the inhibitory effects of the sulfonylureas, whereas eosinophils treated with 1000 pg/mL IL-5 in the presence of glyburide, tolbutamide or glipizide showed a 20 to 30% average decrease in survival. Thus, glyburide is representative of the general effectiveness of sulfonylureas in inhibiting eosinophil survival.

B. Glyburide Inhibits Eosinophil Superoxide Production

Eosinophil activation and degranulation, not their mere presence, are likely critical in initiating the tissue damage associated with eosinophilic inflammation. (Seminario, M. C. and G. J. Gleich, *Curr. Opin. Immunol.* 6:860 (1994)). Activation of eosinophils in vitro can be detected by measuring superoxide production in response to stimuli. It has previously been shown that lidocaine significantly inhibits cytokine-mediated eosinophil superoxide production.

Figure 11A:
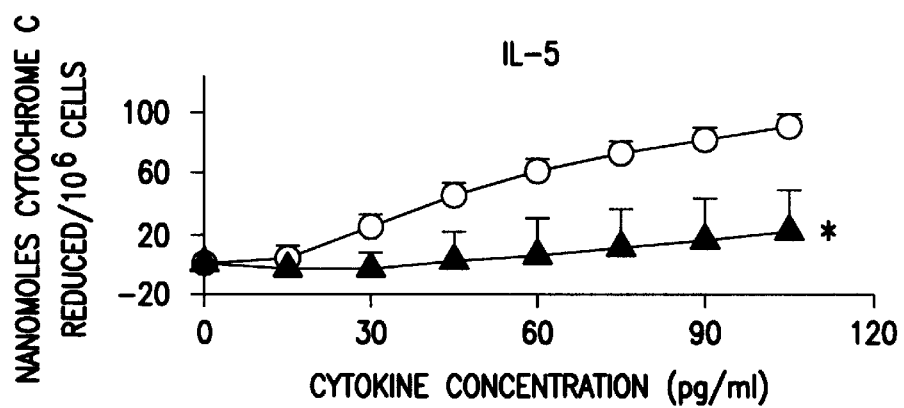
FIG. 11: Graph depicting the inhibitory effect of glyburide on cytokine-mediated superoxide production by eosinophils, as described in Examples V (B) and V (C).
Figure 11B:
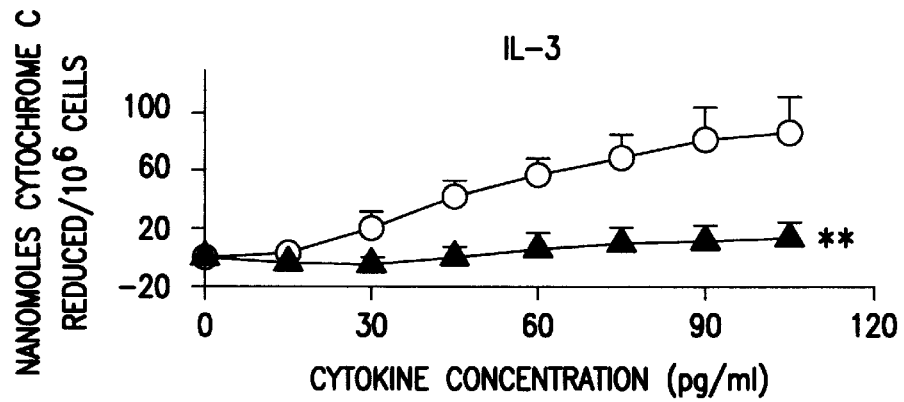
Figure 11C:
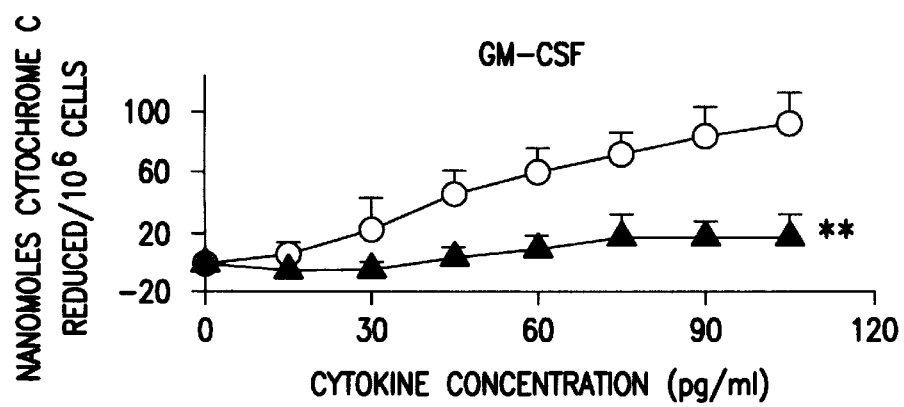

To determine whether glyburide inhibits eosinophil superoxide production, eosinophils were cultured with IL-5, IL-3, or GM-CSF in the presence of glyburide. Purified eosinophils were treated with IL-5, IL-3, or GM-CSF in the presence of medium control (○) or $1 \times 10^{-4}$ M glyburide (▲). Superoxide production was measured as described herein and the results of this experiment are depicted in FIG. 11. Background readings at time zero were subtracted from each time point, and superoxide production was plotted as nanomoles of superoxide produced per million eosinophils versus time. Each panel shows the means (± standard deviations) of at least four independent experiments using eosinophils from both normal and allergic donors. The single asterisk (*) indicates p<0.005; a double asterisk (**) indicates p<0.001 (compared to cytokine stimulation alone at 105 minutes).

The results of this experiment show that all three cytokines stimulated superoxide production by eosinophils. However, superoxide production initiated by the cytokines was dramatically inhibited by glyburide, and excess cytokine did not overcome the inhibition. No preferential inhibition of IL-5 stimulation was seen in the superoxide assay in comparison to the survival assay. Instead, glyburide inhibited superoxide generation induced by all cytokines, including that generated by PAF (data not shown).

C. Synergistic Effects of Lidocaine, Glyburide and Dexamethasone

Lidocaine and glyburide directly inhibit cytokine-mediated eosinophil survival and activation, probably through mechanisms distinct from those of dexamethasone. (Wallen, N., et. al., *J. Immunol.* 147:3490 (1991)) The distinct mechanism hypothesis is supported by the data showing inhibition of IL-5 stimulated survival by glucocorticoids is overcome at a concentration of 1000 pg/ml IL-5 whereas inhibition of IL-5 stimulated survival by glyburide or lidocaine is not overcome at the same concentration of IL-5.

To determine whether lidocaine, glyburide and dexamethasone have any additive or synergistic effects, eosinophils were incubated with IL-5 in the presence of lidocaine, glyburide, or dexamethasone or combinations of these drugs. The results of the eosinophil survival study are depicted in the table shown in FIG. 12.

As shown in FIG. 12, eosinophils treated with lidocaine, glyburide or dexamethasone showed decreased survival at 1000 pg/ml IL-5. All of the combinations showed synergistic activity in the survival assay. Most strikingly, the combination of lidocaine and glyburide essentially abolished the delay of apoptosis induced by IL-5.

Figure 13:
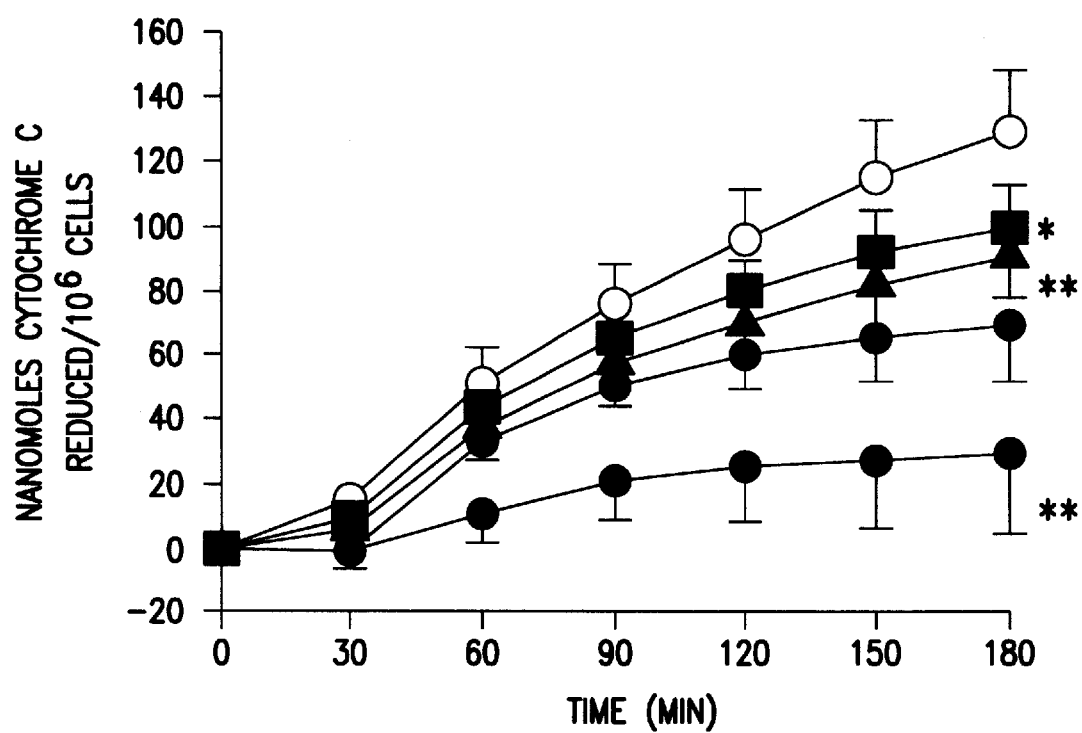
FIG. 13: Graph depicting the synergistic effect of lidocaine and glyburide in blocking IL-5-induced superoxide production, as described in Example V (C).

Eosinophil superoxide production is inhibited by lidocaine and glyburide (FIG. 11), whereas dexamethasone has no effect (data not shown). To determine whether lidocaine and glyburide synergistically block IL-5-induced superoxide production, purified eosinophils were treated with IL-5 in the presence of medium control (○), $3\times10^{-3}$ M lidocaine (■), $1\times10^{-4}$ M glyburide (▲), or a combination of these drugs (●; solid line). The results of this experiment are depicted in FIG. 13. The broken line indicates the predicted additive inhibition of the combination of glyburide and lidocaine. Superoxide production was measured as described herein. Background readings at time zero were subtracted from each time point, and superoxide production was plotted as nanomoles of cytochrome C reduced per million eosinophils versus time. Shown are the means (± standard deviations) of at least five experiments using eosinophils from both normal and allergic donors. The single asterisk (*) indicates $p<0.01$; the double asterisk (**) indicates $p<0.005$ (compared to stimulation with IL-5 alone at 180 minutes).

Treatment of IL-5 stimulated eosinophils with a combination of lidocaine and glyburide results in the synergistic inhibition of superoxide production, as shown in FIG. 13. Combinations of lidocaine or glyburide with dexamethasone did not increase inhibition more that either drug alone (data not shown). This latter result was expected, as dexamethasone does not inhibit eosinophil superoxide production. Thus, the combination of lidocaine plus glyburide synergistically inhibits IL-5 induced superoxide production.

All publications and patents are incorporated by reference herein, as though individually incorporated by reference, as long as they are not inconsistent with the disclosure. The invention is not limited to the exact details shown and described, for it should be understood that many variations and modifications may be made while remaining within the scope of the invention defined by the claims.

What is claimed is:

1. A method for treating a pathology whose symptoms can be counteracted by inhibiting cytokine-induced eosinophil survival or activation in a mammal in need of such treatment comprising administering to said mammal an effective amount of a compound that binds to a sulfonylurea receptor, wherein said compound inhibits cytokine induced eosinophil survival or activation, thereby counteracting said symptoms.

2. A method for treating bronchial asthma, chronic eosinophilic pneumonia, giant papillary conjunctivitis, vernal conjunctivitis, allergic conjunctivitis, allergic rhinitis, allergic sinusitis, eosinophilic gastroenteritis, allergic gastroenteropathy, atopic dermatitis, bullous pemphigoid, episodic angioedema associated with eosinophilia or ulcerative colitis, comprising administering to a mammal in need of such treatment an amount of a compound that binds to a sulfonylurea receptor, wherein said compound inhibits IL-5 induced eosinophil survival or activation.

3. A method for treating bronchial asthma, chronic eosinophilic pneumonia, giant papillary conjunctivitis, vernal conjunctivitis, allergic conjunctivitis, allergic rhinitis, allergic sinusitis, atopic dermatitis, bullous pemphigoid, or episodic angioedema associated with eosinophilia comprising administering to a mammal in need of such treatment an amount of a compound that binds to a sulfonylurea receptor, wherein said compound inhibits IL-5 induced eosinophil survival or activation.

4. A method for treating bronchial asthma comprising administering to a mammal in need of such treatment an amount of a compound that binds to a sulfonylurea receptor, wherein said compound inhibits IL-5 induced eosinophil survival or activation.

5. A method for treating inflammation comprising administering to a mammal in need of such treatment an amount of a compound that binds to a sulfonylurea receptor, wherein said compound inhibits IL-5 induced eosinophil survival or activation.

6. A method for treating bronchial asthma, chronic eosinophilic pneumonia, giant papillary conjunctivitis, vernal conjunctivitis, allergic conjunctivitis, allergic rhinitis, allergic sinusitis, eosinophilic gastroenteritis, allergic gastroenteropathy, atopic dermatitis, bullous pemphigoid, episodic angioedema associated with eosinophilia or ulcerative colitis, comprising administering to a mammal in need of such treatment an amount of a benzenesulfonyl-urea of Formula I:

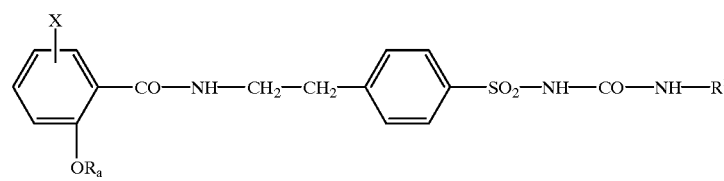

(I)

wherein $R_a$ is lower alkyl or lower alkenyl; X is halogen, lower alkyl, or lower alkoxy; and $R^3$ is cyclohexyl, methylcyclohexyl ethylcyclohexyl, norborn-5-en-2-yl, or norborn-2-yl; or a pharmaceutically acceptable salt thereof; wherein said benzenesulfonyl-urea inhibits IL-5 induced eosinophil survival or activation.

7. A method for treating bronchial asthma, chronic eosinophilic pneumonia, giant papillary conjunctivitis, vernal conjunctivitis, allergic conjunctivitis, allergic rhinitis, allergic sinusitis, atopic dermatitis, bullous pemphigoid, or episodic angioedema associated with eosinophilia comprising administering to a mammal in need of such treatment an amount of a benzenesulfonyl-urea of Formula I:

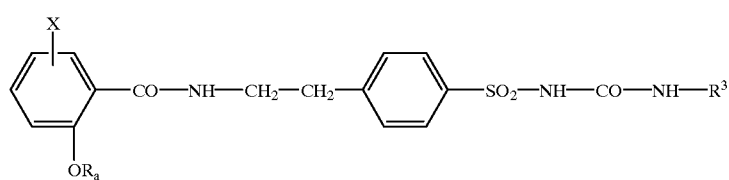

wherein $R_a$ is lower alkyl or lower alkenyl; X is halogen, lower alkyl, or lower alkoxy; and $R^3$ is cyclohexyl, methylcyclohexyl ethylcyclohexyl, norborn-5-en-2-yl, or norbom-2-yl; or a pharmaceutically acceptable salt thereof; wherein said benzenesulfonyl-urea inhibits IL-5 induced eosinophil survival or activation.

8. A method for treating bronchial asthma comprising administering to a mammal in need of such treatment an amount of a benzenesulfonyl-urea of Formula I:

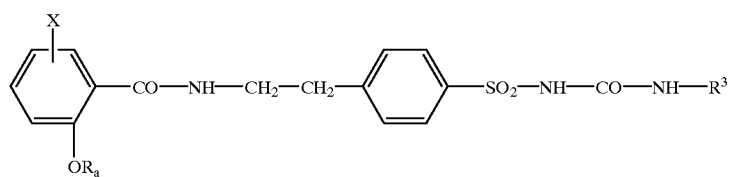

wherein $R_a$ is lower alkyl or lower alkenyl; X is halogen, lower alkyl, or lower alkoxy; and $R^3$ is cyclohexyl, methylcyclohexyl ethylcyclohexyl, norborn-5-en-2-yl, or norborn-2-yl; or a pharmaceutically acceptable salt thereof; wherein said benzenesulfonyl-urea inhibits IL-5 induced eosinophil survival or activation.

9. A method for treating inflammation comprising administering to a mammal in need of such treatment an amount of a benzenesulfonyl-urea of Formula I:

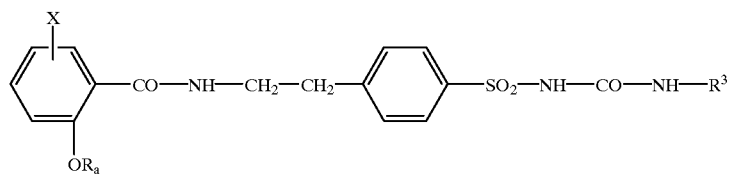

wherein $R_a$ is lower alkyl or lower alkenyl; X is halogen, lower alkyl, or lower alkoxy; and $R^3$ is cyclohexyl, methylcyclohexyl ethylcyclohexyl, norborn-5-en-2-yl, or norborn-2-yl; or a pharmaceutically acceptable salt thereof; wherein said benzenesulfonyl-urea inhibits IL-5 induced eosinophil survival or activation.

10. The method of claim 6, 7, 8, or 9 wherein $R^3$ is 4-methylcyclohexyl or 4-ethylcyclohexyl.

11. The method of claim 6, 7, 8, or 9 wherein X is selected from the group consisting of chloro, methyl, and methoxy; $R_a$ is selected from the group consisting of methyl, ethyl, propyl, isopropyl, butyl, isobutyl, tert butyl, isoamyl, and allyl; and $R^3$ is selected from the group consisting of cyclohexyl, 4-methyl-cyclohexyl, 4-ethylcyclohexyl, norborn-5-en-2-yl, and norborn-2-yl.

12. The method of claim 6, 7, 8, or 9 wherein the compound is glyburide or a pharmaceutically acceptable salt thereof.

13. A method for inhibiting cytokine-induced survival or activation of an eosinophil comprising combining the eosinophil, the cytokine, and an effective inhibitory amount of a compound that binds to a sulfonylurea receptor in vitro.

14. The method of claim 2, 3, 4, or 5 wherein the mammal is a human.

15. The method of claim 2, 3, 4, or 5 wherein the compound is administered in combination with a pharmaceutically acceptable carrier.

16. The method of claim 15 wherein the compound and carrier are administered in a unit dosage form.

17. The method of claim 16 wherein the unit dosage form is adapted for oral administration.

18. The method of claim 16 wherein the unit dosage form is adapted for administration by inhalation.

* * * * *

UNITED STATES PATENT AND TRADEMARK OFFICE
CERTIFICATE OF CORRECTION

PATENT NO. : 6,071,910
DATED : June 6, 2000
INVENTOR(S) : Gleich et al.

Page 1 of 1

It is certified that error appears in the above-identified patent and that said Letters Patent is hereby corrected as shown below:

Column 29
Line 18, delete "norbom" and insert --norborn--, therefor.

Signed and Sealed this

Twelfth Day of June, 2001

*Attest:*

*Attesting Officer*

NICHOLAS P. GODICI
*Acting Director of the United States Patent and Trademark Office*